(12) United States Patent
Abbott et al.

(10) Patent No.: US 7,662,572 B2
(45) Date of Patent: Feb. 16, 2010

(54) COMPOSITIONS AND LIQUID CRYSTALS

(75) Inventors: Nicholas Abbott, Madison, WI (US); Christopher Murphy, Madison, WI (US); Barbara Israel, Mount Horeb, WI (US)

(73) Assignee: Platypus Technologies, LLC., Madison, WI (US)

( * ) Notice: Subject to any disclaimer, the term of this patent is extended or adjusted under 35 U.S.C. 154(b) by 125 days.

(21) Appl. No.: 11/509,898

(22) Filed: Aug. 25, 2006

(65) Prior Publication Data

US 2007/0099249 A1    May 3, 2007

Related U.S. Application Data

(60) Provisional application No. 60/711,111, filed on Aug. 25, 2005.

(51) Int. Cl.
*G01N 33/53* (2006.01)
(52) U.S. Cl. .................. 435/7.1; 435/7.5; 548/303.7; 548/301.7
(58) Field of Classification Search .................. None
See application file for complete search history.

(56) References Cited

U.S. PATENT DOCUMENTS

| | | | |
|---|---|---|---|
| 2,639,815 A | 5/1953 | Paluck | |
| 3,645,693 A | 2/1972 | Poziomek et al. | |
| 3,883,398 A | 5/1975 | Ono | |
| 3,910,763 A | 10/1975 | Poziomek et al. | |
| 4,068,925 A | 1/1978 | Tani et al. | |
| 4,096,086 A | 6/1978 | Kanbe et al. | |
| 4,285,697 A | 8/1981 | Neary et al. | |
| 4,551,264 A | 11/1985 | Eidenschink et al. | |
| 4,597,942 A | 7/1986 | Meathrel et al. | |
| 4,612,873 A | 9/1986 | Eberle | |
| 4,795,253 A | 1/1989 | Sandridge et al. | |
| 4,927,879 A | 5/1990 | Pidgeon | |
| 5,059,394 A | 10/1991 | Phillips et al. | |
| 5,073,294 A | 12/1991 | Shannon et al. | |
| 5,132,226 A | 7/1992 | Dreher et al. | |
| 5,141,718 A | 8/1992 | Clark et al. | |
| 5,298,394 A | 3/1994 | Arima et al. | |
| 5,355,215 A | 10/1994 | Schroeder et al. | |
| 5,370,841 A | 12/1994 | McDonnel et al. | |
| 5,474,796 A | 12/1995 | Brennan | |
| 5,599,919 A | 2/1997 | Yen et al. | |

(Continued)

FOREIGN PATENT DOCUMENTS

GB          2297549 A    *  8/1996

(Continued)

OTHER PUBLICATIONS

Goodby et al. (Angew. Chem. Int. Ed. 2008, 47, 2754-2787.*

(Continued)

*Primary Examiner*—Kamal A Saeed
*Assistant Examiner*—Valerie Rodriguez-Garcia
(74) *Attorney, Agent, or Firm*—Casimir Jones, S.C.

(57) ABSTRACT

The present invention relates to compounds, compositions, and methods in the field of detection of analytes. In particular to detection of viruses, cells, bacteria, lipid-membrane containing organisms, proteins, nucleic acids, carbohydrates and other biomolecules, organic molecules and inorganic molecules using a liquid crystal assay format.

13 Claims, 5 Drawing Sheets

U.S. PATENT DOCUMENTS

| | | |
|---|---|---|
| 5,601,980 A | 2/1997 | Gordon et al. |
| 5,700,637 A | 12/1997 | Southern |
| 5,858,659 A | 1/1999 | Sapolsky et al. |
| 5,908,786 A | 6/1999 | Moreno et al. |
| 5,925,525 A | 7/1999 | Fodor et al. |
| 5,985,551 A | 11/1999 | Brennan |
| 6,001,311 A | 12/1999 | Brennan |
| 6,017,696 A | 1/2000 | Heller |
| 6,040,193 A | 3/2000 | Winkler et al. |
| 6,045,996 A | 4/2000 | Cronin et al. |
| 6,051,380 A | 4/2000 | Sosnowski et al. |
| 6,068,818 A | 5/2000 | Ackley et al. |
| 6,171,780 B1 | 1/2001 | Pham et al. |
| 6,171,802 B1 * | 1/2001 | Woolverton et al. ......... 435/7.1 |
| 6,201,588 B1 | 3/2001 | Walton et al. |
| 6,242,266 B1 | 6/2001 | Schleifer et al. |
| 6,277,489 B1 | 8/2001 | Abbott et al. |
| 6,277,490 B1 | 8/2001 | Ruf |
| 6,284,197 B1 * | 9/2001 | Abbott et al. ............ 422/82.05 |
| 6,288,392 B1 | 9/2001 | Abbott et al. |
| 6,306,659 B1 | 10/2001 | Parce et al. |
| 6,444,254 B1 | 9/2002 | Chilkoti et al. |
| 6,468,657 B1 | 10/2002 | Hou et al. |
| 6,586,257 B1 | 7/2003 | Vuong |
| 6,596,545 B1 | 7/2003 | Wagner et al. |
| 6,692,699 B2 | 2/2004 | Abbott et al. |
| 6,780,492 B2 | 8/2004 | Abbott |
| 6,797,463 B2 | 9/2004 | Abbott et al. |
| 6,824,837 B2 | 11/2004 | Abbott |
| 6,844,184 B2 | 1/2005 | Kim et al. |
| 6,849,321 B2 | 2/2005 | Abbott et al. |
| 6,852,285 B2 | 2/2005 | Abbott et al. |
| 6,858,423 B1 | 2/2005 | Abbott et al. |
| 6,884,357 B2 | 4/2005 | Siddiqi |
| 7,018,838 B2 | 3/2006 | Murphy et al. |
| 7,125,592 B2 | 10/2006 | Abbott |
| 7,135,143 B2 | 11/2006 | Abbott |
| 7,303,694 B2 | 12/2007 | Abbott |
| 7,371,563 B2 | 5/2008 | Duffy et al. |
| 2002/0004216 A1 | 1/2002 | Abbott et al. |
| 2002/0028451 A1 | 3/2002 | Abbott et al. |
| 2002/0052002 A1 | 5/2002 | Niehaus et al. |
| 2002/0055093 A1 | 5/2002 | Abbott et al. |
| 2002/0123134 A1 | 9/2002 | Huang et al. |
| 2002/0142453 A1 | 10/2002 | Abbott et al. |
| 2002/0164604 A1 | 11/2002 | Abbott et al. |
| 2002/0172621 A1 | 11/2002 | Barbera-Guillem |
| 2002/0173033 A1 | 11/2002 | Hammerick et al. |
| 2003/0032046 A1 | 2/2003 | Duffy et al. |
| 2003/0049468 A1 | 3/2003 | Hu et al. |
| 2003/0071949 A1 | 4/2003 | Abbott |
| 2003/0099993 A1 | 5/2003 | Abbott et al. |
| 2003/0124029 A1 | 7/2003 | Webb et al. |
| 2003/0127396 A1 | 7/2003 | Siddiqi |
| 2003/0180966 A1 | 9/2003 | Abbott |
| 2003/0194753 A1 | 10/2003 | Abbott |
| 2004/0002131 A1 | 1/2004 | Kim et al. |
| 2004/0009583 A1 | 1/2004 | Benn et al. |
| 2004/0038408 A1 | 2/2004 | Abbott et al. |
| 2004/0091620 A1 | 5/2004 | Abbott |
| 2004/0142411 A1 | 7/2004 | Kirk et al. |
| 2004/0161800 A1 | 8/2004 | Abbott et al. |
| 2004/0224380 A1 | 11/2004 | Chou et al. |
| 2005/0064395 A1 | 3/2005 | Israel et al. |
| 2005/0079486 A1 | 4/2005 | Abbott |
| 2005/0079487 A1 | 4/2005 | Abbott |
| 2005/0106562 A1 | 5/2005 | Abbott |
| 2005/0112544 A1 | 5/2005 | Xu et al. |
| 2005/0221271 A1 | 10/2005 | Abbott |
| 2005/0260703 A1 | 11/2005 | Abbott |
| 2006/0003389 A1 | 1/2006 | Abbott |
| 2006/0141446 A1 | 6/2006 | Abbott |
| 2006/0252031 A1 | 11/2006 | Abbott |
| 2007/0004046 A1 | 1/2007 | Abbott |
| 2007/0042505 A1 | 2/2007 | Abbott |
| 2007/0099249 A1 | 5/2007 | Abbott |
| 2007/0104612 A1 | 5/2007 | Abbott |
| 2007/0110614 A1 | 5/2007 | Abbott |
| 2007/0231832 A1 | 10/2007 | Abbott |
| 2007/0269848 A1 | 11/2007 | Abbott |
| 2008/0050799 A1 | 2/2008 | Abbott |
| 2008/0160539 A1 | 7/2008 | Abbott |
| 2008/0187949 A1 | 8/2008 | Goldbard et al. |
| 2009/0054262 A1 | 2/2009 | Abbott et al. |

FOREIGN PATENT DOCUMENTS

| | | |
|---|---|---|
| WO | WO 91/18653 A2 | 12/1991 |
| WO | WO 99/63329 | 6/1999 |
| WO | WO 00/50570 A2 | 8/2000 |
| WO | WO 01/61325 A2 | 2/2001 |
| WO | WO 01/61325 A3 | 2/2001 |
| WO | WO 01/61357 A2 | 2/2001 |
| WO | WO 03/019191 | 7/2002 |
| WO | WO 02/071929 A2 | 9/2002 |
| WO | WO 02/075294 | 9/2002 |
| WO | WO 03/021339 A2 | 9/2002 |
| WO | WO 03/029481 | 4/2003 |
| WO | WO 03/081230 | 10/2003 |
| WO | WO 03/086197 | 10/2003 |
| WO | WO 2004/041061 | 5/2004 |
| WO | WO 2004/044583 | 5/2004 |
| WO | WO 05/010160 | 7/2004 |

OTHER PUBLICATIONS

Gupta et al, "Optical Amplification of Ligand-Receptor Binding Using Liquid Crystals," Science vol. 279, Mar. 27, 1998 pp. 2077-2080.

Green et al., "Mechanism of the Transformation of a Stiff Polymer Lyotropic Nematic Liquid Crystal to the Cholesteric State by Dopant-Mediated ChiralInformation Transfer", J. Am. Chem. Soc., 1998. 120,9810-9817.

Seung Ryeol Kim et al. Anal. Chem "A Possible Substrate for Biomolecular Assays Based on Liquid Crystals, Analytical 2 Chemistry,"(2000) 72(19);4646-4653.

Lauer L. et al, "Spot Complaint Neuronal Networks by Structure Optimized Micro-Contact Printing" Biomaterials, Elsevier Science, 2001, vol. 22, pp. 1925-1932.

Kikuchi H E et al, "Culture of Bone-Marrow-Derived Cells in Microfabricated Pit Arrays" Proc SPIE Int Soc Opt Eng; 2001, vol. 4265, pp. 40-49.

Iwuoha E I et al: Reactivities of Organic Phase Biosensors 3: Electrochemical Study of Cytochrome P450 CAM Immobilized in a Methyltriethoysilane SOL-GEL Electroanalysis, VHC Publishers Inc. ( 2000) vol. 12, p. 980.

Skaife, Justin G et al. "Quantitative Interpretation of the Optical Textures of Liquid Crystals Caused by Specific Binding of Immunoglobulins to Surface-Bound Antugens," Langmuir (2000) 16(7):3529-3536.

Skaife, Justin G et al, "Quanitative Characterization of Obliquely Deposited Subtrates of Gold by Atomic Force Microscopy: Influence of Substrate Topography on Anchoring of Liquid Crystals" Chemistry of Materials, V 11(3) 1999, pp. 612-623.

Vinay K. Gupta et al. "Using Droplets of Nematic Liquid Crystal To Probe the Microscopic and Mesoscopic Structure of Organic Surfaces," Langmuir 15:21 (1999) 7213-7223.

R. R. Shah et al. "Principles for Measurement of Chemical Exposure Based on Recognition-Driven Anchoring Transitions in Liquid Crystals," Science (2001) 393(5533):1296-99.

Kleinfeld D. et al., "Controlled Outgrowth of Dissociated Neurons on Patterned Substrates," J. Neurosci. (1998) 8:4098 120.

Kumar et al. "Patterned Self-Assembled Monolayers and Meso-Scale Phenomena," Langmuir (1994) 10:1498 511.

Xia Y, "Use of Controlled Reactive Spreading of Liquid Alkanethiol OD the Surface of Gold To Modify the Size of Features Produced by Mierocontact Printing," Whitesides, G., J. Am. Chern. Soc. (1995) 117:327475.

Hickman et al.,"Rational pattern design for in vitro cellular networks using surface photochemistry," J. Vac. Sci. Technol. (1994) 12:607 16.

Jerome, Blandine, "Surface effects and anchoring in liquid crystals," Rep. Prog. Phys. (1991) 54:391 451.

Gupta et al. Design of Surfaces for Patterned Alignment of liquid Crystals on Planar and Curved Substrates, Science (1997) 276:1533-1536.

Drawhorn et al, "Anchoring of Nematic Liquid Crystals on Self-Assembled Monolayers Formed from Alkanethiols on Semitransparent Films of Gold," J. Phys. Chem. (1995) 45:16511.

Ladam, Guy et al, "Protein Adsorption onto Auto-Assembled Polyelectrolyte Films," Langmuir (2001) 17(3):878-882.

Wagner et al "Covalent Immobilization of Native Biomolecules onto Au(111} via N-Hydroxysuccinimide Ester Functionalized Self-Assembled Monolayers for Scanning Probe Microscopy," Biophys. J. (1996) 70:2052 2066.

Tarlov et al.,"UV Photopatterning of Alkanethiolate Monolayers," J. Am. Chem. Soc (1993) 115: 5305.

Kumar et al, "Patterned Self-Assembled Monolayers and Meso-Scale Phenomena," Acc. Chem. Res. (1995) 28: 219.

Resler D. P et al, "High-efficiency liquid-crystal optical phased-array beam steering," Opt. Lett. (1996) 21, 689.

Stern, Margaret B, "Binary Optics: A VLSI-based microoptics technology," Microelectron. Eng. (1996) 32. 369.

Goto et al, "Design of an Aberration-Free Spherical Micro Lens with a Diffractive Relief Grating Film on a Refractive Spherical Glass Substrate," Jpn. J. AppL Phys. (1992) 31,1586.

Magiera et al,"Hybrid Imaging Element—Possibilities of Aberration Correction," Soc. Photo Opt. lnstrum. Eng., (1996) 2774, 204.

Bernard, et al. Affinity capture of proteins from solution and their dissociation by contact printing. Nature Biotechnology. 2001; 19(9):866-869.

Renault et al. "Fabricating Microarrays of Functional Proteins Using Affinity Contact Printing." Angew. Chem. Int. Ed. 2002; 41 (13):2320-2323.

Fast, Cheap, Portable: A New Pathogen Detection Tool. Biomedical Instrumentation & Technology.2002; 36(1): 15.

Woolverton, et al. A liquid crystal biosensor for virus detection. Abstracts of the General Meeting of the American Society for Microbiology. 2002;102:110-111. (Abstract Only) (1 PG.).

Espinopza LA, Schumann KR, Luk YY, Israel BA, Abbott NL; Orientational Behavior of Thermotropic Liquid Crystals On Surfaces Presenting Electrostatically Bound Vesicular Stomatitis Virus. Langmuir Mar. 16, 2004; 20(6):2375-85.

Tingey et al. "Imaging of Affinity Microcontact Printed Proteins by Using Liquid Crystals." Langmuir.2004; 20:6816-6826.

* cited by examiner

N-[4'-cyanobiphen-4-yl] lysine

COMPOSITIONS AND LIQUID CRYSTALS

This application claims the benefit of U.S. Prov. Appl. No. 60/711,111, file Aug. 25, 2005, which is incorporated herein in its entirety.

BACKGROUND

The technology relates to the field of liquid crystal compositions. Methods for detecting the presence of biological substances and chemical compounds in samples have been an area of continuous development in the field of analytical chemistry and biochemistry. Although ELISA and other immunosorbent assays are widely used methods, they have several disadvantages and there is a need for improvement. Among the desired attributes are: lower cost, less reliance on use of labile, expensive reagents, less complexity in execution, decreased hands-on time required for processing the sample and execution of the assay, minimal technical proficiency for running assays and interpreting results, miniaturization and portability of equipment, automation, and an increase in multiplexing capability.

SUMMARY OF THE INVENTION

The present invention relates to compounds, compositions, and methods in the field of detection of analytes. In particular to detection of viruses, cells, bacteria, lipid-membrane containing organisms, proteins, nucleic acids, carbohydrates and other biomolecules, organic molecules and inorganic molecules using a liquid crystal assay format.

In some embodiments, a compound comprises a recognition moiety substituted with a mesogen substituent. In further embodiments, the mesogen is an amino acid sequence. In further embodiments the recognition moiety is an amino acid sequence.

In some embodiments, a liquid crystal composition comprises: a first compound comprising: a recognition moiety substituted with a mesogen substituent and a recognition moiety; and a second compound comprising said mesogen. In further embodiments, the recognition moiety is biotin. In further embodiments, the mesogen is 5,5'-[(2-hydroxytrimethylene)dioxy]bis(4-oxo-4H-1-benzopyran-2-carboxylic acid). In further embodiments, the mesogen is 4'-alkyl-(1,1'-Biphenyl)-4-carbonitrile. In further embodiments, the mesogen is 5,5'-[(2-hydroxytrimethylene)dioxy]bis(4-oxo-4H-1-benzopyran-2-carboxylic acid) and the recognition moiety is an amino acid sequence. In further embodiments, the composition further comprises a metal salt. In further embodiments, said metal is selected from the group consisting of copper, indium, and chromium.

In some embodiments, a liquid crystal composition comprises lysozyme substituted with a biotin substituent.

In some embodiments, a device comprises: a) a substrate comprising avidin and b) a liquid crystal composition comprising lysozyme substituted with a biotin substituent.

In some embodiments, a device comprises: a) a substrate comprising a ligand; b) a liquid crystal composition comprising i) a recognition moiety wherein said recognition moiety binds to said ligand; and ii) a linking agent wherein the linking agent covalently couples to said recognition moiety. In further embodiments, said ligand is an antigen and said recognition moiety is an antibody. In further embodiments, said linking agent is an activated dicarboxylic acid.

In some embodiments, a method of making a device comprises: a) providing: i) substrate comprising a ligand; ii) a liquid crystal comprising; 1) an recognition moiety wherein said recognition moiety binds to said ligand; and b) a linking agent wherein said linking agent covalently couples to said recognition moiety; c) contacting said liquid crystal with said substrate; and d) contacting said linking agent with said liquid crystal composition.

In some embodiments, a device comprises: a) an optically transparent substrate; b) a liquid crystal composition comprising a detection region comprising a recognition moiety; and c) a series of parallel lines.

In some embodiments, a detection method comprises: a) providing: i) an analyte; ii) an device comprising: 1) an optically transparent substrate; 2) a liquid crystal composition comprising a detection region comprising a recognition moiety; and 3) a first line and a second line; wherein said recognition moiety binds with said analyte b) contacting said analyte with said device; and c) attempting to detect said first line and said second line. In further embodiments, said analyte is a pesticide. In further embodiments, said first line and said second line are parallel.

In some embodiments, an amino acid arrangement is substituted with a mesogen substituent. In further embodiments, the mesogen is 4'-cyanobiphen-4-yl. In some embodiments, a protein comprises an amino acid arrangement substituted with a mesogen substituent. In further embodiments, said amino acid arrangement is selected from the side chain group consisting of 4'-cyanobiphen-4-yllysine and 4'-cyanobiphen-4-ylalanine.

In some embodiments, a liquid crystal composition comprises an amino acid substituted with a mesogen substituent. In further embodiments, said amino acid is selected from the side chain group consisting of 4'-cyanobiphen-4-yllysine and 4'-cyanobiphen-4-ylalanine.

In some embodiments, a compound comprises: a chemical structure substantially identical to a mesogen and a recognition moiety. In further embodiments, the mesogen is an amino acid sequence, and in further embodiments the recognition moiety is an amino acid sequence.

In some embodiments, a composition comprises: a compound comprising: a chemical structure substantially identical to a mesogen and a recognition moiety; and said mesogen. In further embodiments, the recognition moiety is biotin. In further embodiments, the mesogen is 5,5'-[(2-hydroxytrimethylene)dioxy]bis(4-oxo-4H-1-benzopyran-2-carboxylic acid). In further embodiments, the mesogen is 4'-alkyl-(1,1'-Biphenyl)-4-carbonitrile. In further embodiments, the mesogen is 5,5'-[(2-hydroxytrimethylene)dioxy]bis(4-oxo-4H-1-benzopyran-2-carboxylic acid) and the recognition moiety is an amino acid sequence. In further embodiments, the composition further comprises a metal salt. In further embodiments said metal is selected from the group consisting of copper, indium, and chromium.

In some embodiments, a liquid crystal composition comprises biotinylated lysozyme. In some embodiments, a cell comprises: a substrate comprising avidin and a liquid crystal comprising a biotinylated lysozyme.

In some embodiments, a cell comprises: a substrate comprising a ligand; a liquid crystal composition comprising an recognition moiety wherein said recognition moiety binds to said ligand; and a linking agent wherein the linking agent covalently couples to said recognition moiety. In further embodiments said ligand is an antigen and said recognition moiety is an antibody. In further embodiments said linking agent is an activated dicarboxylic acid.

In some embodiments, a method of making a cell comprises: providing: a substrate comprising a ligand; a liquid crystal comprising; an recognition moiety wherein said recognition moiety binds to said ligand; and a linking agent wherein said linking agent covalently couples to said recognition moiety; contacting said liquid crystal with said substrate; and contacting said linking agent with said liquid crystal composition.

In some embodiments, a cell comprises an optically transparent substrate; a liquid crystal composition comprising a detection region comprising a recognition moiety; and a series of parallel lines.

In some embodiments, a detection method comprises: providing: an analyte; an cell comprising: an optically transparent substrate; a liquid crystal composition comprising a detection region comprising a recognition moiety; and a first line and a second line; wherein said recognition moiety binds with said analyte contacting said analyte with said cell; and attempting to detect said first line and said second line. In further embodiments, said analyte is a pesticide. In further embodiments, said first line and said second line are parallel.

In some embodiments, an amino acid is substituted with a mesogen. In further embodiments said mesogen is 4'-cyanobiphen-4-yl. In some embodiments, a protein comprises an amino acid substituted with a mesogen. In further embodiments said amino acid is selected from the group consisting of 4'-cyanobiphen-4-yllysine and 4'-cyanobiphen-4-ylalanine.

In some embodiments, a liquid crystal composition comprises an amino acid substituted with a mesogen. In further embodiments, said amino acid is selected from the group consisting of 4'-cyanobiphen-4-yllysine and 4'-cyanobiphen-4-ylalanine.

DEFINITIONS

Figure 1:
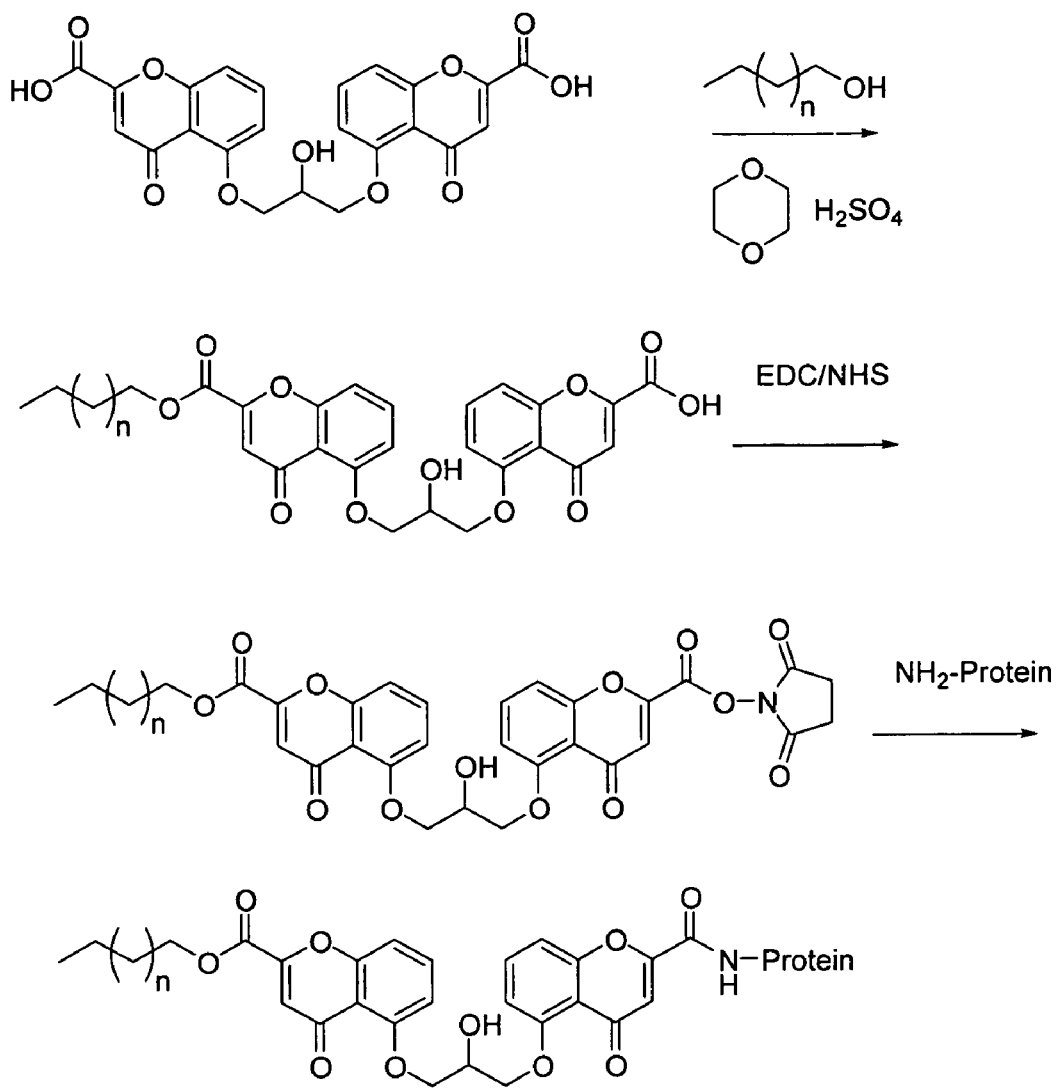
FIG. 1. This is a scheme for the preparation of a protein coupled to the mesogen, 5,5'-[(2-hydroxytrimethylene)dioxy]bis(4-oxo-4H-1-benzopyran-2-carboxylic acid).

As used herein, the term "chemical structure" and the like refer to an atomic arrangement of elements. It is appreciated that changes in atom arrangement can be made that do not substantially alter major physical properties of the molecule. Physical properties include binging interactions. For example, a hydrogen atom may be omitted in order to substitute another chemical structure without altering the ability of the chemical structure to act as a recognition moiety or ligand.

As used herein, the term "amino acid" means a compound containing an amino group ($NH_2$), a carboxylic acid group (COOH), and any of various side groups, including compounds that have the basic formula $NH_2CHRCOOH$ wherein R is a side group that can be any chemical structure.

The term "amino acid arrangement" refers to a chemical structure containing a first nitrogen connected to a first carbon wherein said first carbon is in a sp3 hybridization state; the first carbon is connected to a second carbon, wherein said second carbon is in an sp2 hybridization state; said second carbon is connected to a first oxygen; and said second carbon is connected to an atom selected from the group consisting of a sulfur, a second oxygen and a second nitrogen.

The term "amino acid sequence" means chemical structures with two or more amino acid arrangements. For example, amino acid sequence includes multiple amino acid arrangements that are linked together by peptide bonds to form proteins including those that function as chemical messengers and as intermediates in metabolism.

The term "substituted" as used herein means that a chemical structure in which at least one hydrogen, oxygen, or nitrogen atom is replaced with a substituent. In the case of an oxo substituent ("=O"), two hydrogen atoms are replaced. "Substituents" within the context of this invention include halogen, hydroxy, oxo, cyano, nitro, amino, alkylamino, dialkylamino, alkyl, alkoxy, alkylthio, haloalkyl, aryl, arylalkyl, heteroaryl, heteroarylalkyl, heterocycle and heterocyclealkyl, as well as $-NR_aR_b$, $-NR_aC(=O)R_b$, $-NR_aC(=O)NR_aR_b$, $-NR_aC(=O)OR_b$, $-NR_aSO_2R_b$, $C(=O)R_a$, $-C(=O)OR_a$, $-C(=O)NR_aR_b$, $-OR_a$, $-SR_a$, $-SOR_a$, $-S(=O)_2R_a$, $-OS(=O)_2R_a$ and $-S(=O)_2OR_a$. In addition, the above substituents may be further substituted with one or more of the above substituents, and so on. $R_a$ and $R_b$ in this context may be the same or different and independently hydrogen, alkyl, haloalkyl, substituted alkyl, aryl, substituted aryl, arylalkyl, substituted arylalkyl, heterocycle, substituted heterocycle, heterocyclealkyl or substituted heterocyclealkyl.

"Alkyl" means a straight chain or branched, noncyclic or cyclic, unsaturated or saturated aliphatic hydrocarbon containing from 1 to 10 carbon atoms, while the term "lower alkyl" has the same meaning as alkyl but contains from 1 to 6 carbon atoms. The term "higher alkyl" has the same meaning as alkyl but contains from 2 to 10 carbon atoms. Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like. Representative saturated cyclic alkyls include cyclopropyl, cyclobutyl, cyclopentyl, cyclohexyl, and the like; while unsaturated cyclic alkyls include cyclopentenyl and cyclohexenyl, and the like. Cyclic alkyls are also referred to herein as a "homocycles" or "homocyclic rings." Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

"Aryl" means an aromatic carbocyclic moiety such as phenyl or naphthyl.

"Arylalkyl" means an alkyl having at least one alkyl hydrogen atoms replaced with an aryl moiety, such as benzyl, $-(CH_2)_2$ phenyl, $-(CH_2)_3$ phenyl, $-CH(phenyl)_2$, and the like.

"Heteroaryl" means an aromatic heterocycle ring of 5- to 10 members and having at least one heteroatom selected from nitrogen, oxygen and sulfur, and containing at least 1 carbon atom, including both mono- and bicyclic ring systems. Representative heteroaryls are furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl.

"Heteroarylalkyl" means an alkyl having at least one alkyl hydrogen atom replaced with a heteroaryl moiety, such as —CH$_2$pyridinyl, —CH$_2$pyrimidinyl, and the like.

"Heterocycle" (also referred to herein as a "heterocyclic ring") means a 4- to 7-membered monocyclic, or 7- to 10-membered bicyclic, heterocyclic ring which is either saturated, unsaturated, or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring. The heterocycle may be attached via any heteroatom or carbon atom. Heterocycles include heteroaryls as defined above. Thus, in addition to the heteroaryls listed above, heterocycles also include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

"Heterocyclealkyl" means an alkyl having at least one alkyl hydrogen atom replaced with a heterocycle, such as —CH$_2$morpholinyl, and the like.

"Homocycle" (also referred to herein as "homocyclic ring") means a saturated or unsaturated (but not aromatic) carbocyclic ring containing from 3-7 carbon atoms, such as cyclopropane, cyclobutane, cyclopentane, cyclohexane, cycloheptane, cyclohexene, and the like.

"Halogen" means fluoro, chloro, bromo and iodo.

"Haloalkyl" means an alkyl having at least one hydrogen atom replaced with halogen, such as trifluoromethyl and the like.

"Alkoxy" means an alkyl moiety attached through an oxygen bridge (i.e., —O-alkyl) such as methoxy, ethoxy, and the like.

"Alkylthio" means an alkyl moiety attached through a sulfur bridge (i.e., —S-alkyl) such as methylthio, ethylthio, and the like.

"Alkylsulfonyl" means an alkyl moiety attached through a sulfonyl bridge (i.e., —SO$_2$-alkyl) such as methylsulfonyl, ethylsulfonyl, and the like.

"Alkylamino" and "dialkylamino" mean one or two alkyl moiety attached through a nitrogen bridge (i.e., —N-alkyl) such as methylamino, ethylamino, dimethylamino, diethylamino, and the like.

The term "activated group" and the like (e.g. activated dicarboxylic acid), means the chemical structure of the group is substituted with a leaving group substituent.

A "coupling catalyst" means a molecular entity that temporarily interacts with a molecule after displacing a leaving group until the entity is itself displaced by a nucleophile. For example, pyridine or dimethylamino pyridine are routinely uses as carboxylic acid coupling catalyst because the pyridine reacts with activated carbonyls and is itself displaced by other nucleophiles (i.e., alcohols, amines, etc.)

"Exposing" or "deprotecting" a first atom, and the like, means breaking chemical bonds between the first atom and a second atom in a chemical structure intended to prevent modification of the first atom until exposure to a selected deprotecting reagent.

A "leaving group" means a molecular arraignment that creates higher relative reactivity by shifting electron density away from a reactive site causing nucleophiles to bond with the reactive site and break bonds with the leaving group. For example, the chlorine of an acid chloride shifts electron density away from the carbon of the carbonyl group increasing the carbonyl's carbon reactivity to alcohols that will form bonds between the oxygen the carbonyl's carbon and break the bond to the chlorine. There are many leaving groups known to those skilled in the art.

A "leaving group reagent" means a reagent used with the intent to introduce leaving groups into molecules.

"Modification" of an atom means adding a new chemically bonded atom to said atom, eliminating the atom, and/or reducing or oxidizing the atomic hybridization state (i.e., sp$^2$ to an sp$^3$, reduction, or sp$^3$ to an sp, oxidation).

A "nucleophile" (or nucleophilic reagent) is a reagent that forms a bond to its reaction partner by donating bonding electrons.

As used herein, the term "recognition moiety" refers to a composition of matter that interacts with an analyte of interest in either a covalent or noncovalent manner.

As used herein, the term "virus recognition moiety" refers to any composition of matter that binds specifically to a virus. Examples of "virus recognition moieties" include, but are not limited to antigen binding proteins and nucleic acid aptamers.

As used herein, the term "analyte" refers to a substance or chemical constituent that is undergoing analysis.

As used herein, the term "ligand" refers to any molecule that binds to or can be bound by another molecule. A ligand is any ion, molecule, molecular group, or other substance that binds to another entity to form a larger complex. Examples of ligands include, but are not limited to, peptides, carbohydrates, nucleic acids, antibodies, or any molecules that bind to receptors.

As used herein, the term "homeotropic director" refers to a topographical feature (e.g., a nanostructure or homeotropic orienting polyimide) of a substrate that homeotropically orients a liquid crystal.

As used herein, the term "pathogen" refers to disease causing organisms, microorganisms, or agents including, but not limited to, viruses, bacteria, parasites (including, but not limited to, organisms within the phyla Protozoa, Platyhelminthes, Aschelminthes, Acanthocephala, and Arthropoda), fungi, and prions.

As used herein, the term "bacteria" and "bacterium" refer to all prokaryotic organisms, including those within all of the phyla in the Kingdom Procaryotae. It is intended that the term encompass all microorganisms considered to be bacteria including *Mycoplasma, Chlamydia, Actinomyces, Streptomyces*, and *Rickettsia*. All forms of bacteria are included within this definition including cocci, bacilli, spirochetes, spheroplasts, protoplasts, etc. "Gram negative" and "gram positive" refer to staining patterns obtained with the Gram-staining process which is well known in the art (See e.g., Finegold and Martin, Diagnostic Microbiology, 6th Ed. (1982), CV Mosby St. Louis, pp 13-15).

As used herein, the term "lipid membrane" refers to, in its broadest sense, a thin sheet or layer comprising lipid molecules. It is intended that the term encompass all "biomembranes" (i.e., any organic membrane including, but not limited to, plasma membranes, nuclear membranes, organelle membranes, and synthetic membranes). Typically, membranes are composed of lipids, proteins, glycolipids, steroids, sterol and/or other components. As used herein, the term "membrane fragment" refers to any portion or piece of a membrane.

As used herein, the term "lipid" refers to a variety of compounds that are characterized by their solubility in organic solvents. Such compounds include, but are not limited to, fats, waxes, steroids, sterols, glycolipids, glycosphingolipids (including gangliosides), phospholipids, terpenes, fat-soluble vitamins, prostaglandins, carotenes, and chlorophylls. As used herein, the phrase "lipid-based materials" refers to any material that contains lipids.

As used herein, the term "liposome" refers to artificially produced spherical lipid complexes that can be induced to segregate out of aqueous media.

As used herein, the term "secondary binding agent" refer to a molecule or collection of molecules that binds to one of an analyte-recognition moiety complex. It is contemplated that secondary binding agents are useful for amplifying the signal resulting from analyte-recognition moiety binding.

As used herein, the term "column media" refers to media used to fill a chromatography column, such as cationic exchange media, anionic exchange media, and immunoaffinity column media.

As used herein, the term "detection region" refers to a discreet area on substrate that is designated for detection of an analyte (e.g., a virus of interest) in a sample.

As used herein, the term "immobilization" refers to the attachment or entrapment, either chemically or otherwise, of a material to another entity (e.g., a solid support) in a manner that restricts the movement of the material.

As used herein, the terms "material" and "materials" refer to, in their broadest sense, any composition of matter.

As used herein the term "antigen binding protein" refers to a glycoprotein evoked in an animal by an immunogen (antigen) and to proteins derived from such glycoprotein (e.g., single chain antibodies and F(ab')2, Fab' and Fab fragments). An antibody demonstrates specificity to the immunogen, or, more specifically, to one or more epitopes contained in the immunogen. Native antibody comprises at least two light polypeptide chains and at least two heavy polypeptide chains. Each of the heavy and light polypeptide chains contains at the amino terminal portion of the polypeptide chain a variable region (i.e., VH and VL respectively), which contains a binding domain that interacts with antigen. Each of the heavy and light polypeptide chains also comprises a constant region of the polypeptide chains (preferably the carboxy terminal portion) which may mediate the binding of the immunoglobulin to host tissues or factors influencing various cells of the immune system, some phagocytic cells and the first component (C1q) of the classical complement system. The constant region of the light chains is referred to as the "CL region," and the constant region of the heavy chain is referred to as the "CH region." The constant region of the heavy chain comprises a CH1 region, a CH2 region, and a CH3 region. A portion of the heavy chain between the CH1 and CH2 regions is referred to as the hinge region (i.e., the "H region"). The constant region of the heavy chain of the cell surface form of an antibody further comprises a spacer-transmembranal region (M1) and a cytoplasmic region (M2) of the membrane carboxy terminus. The secreted form of an antibody preferably lacks the M1 and M2 regions.

As used herein, the term "selective binding" refers to the binding of one material to another in a manner dependent upon the presence of a particular molecular structure (i.e., specific binding). For example, an immunoglobulin will selectively bind an antigen that contains the chemical structures complementary to the ligand binding site(s) of the immunoglobulin. This is in contrast to "non-selective binding," whereby interactions are arbitrary and not based on structural compatibilities of the molecules.

As used herein, the term "polymerization" encompasses any process that results in the conversion of small molecular monomers into larger molecules consisting of repeated units. Typically, polymerization involves chemical crosslinking of monomers to one another.

As used herein, the term "antigen" refers to any molecule or molecular group that is recognized by at least one antibody. By definition, an antigen must contain at least one epitope (i.e., the specific biochemical unit capable of being recognized by the antibody). The term "immunogen" refers to any molecule, compound, or aggregate that induces the production of antibodies. By definition, an immunogen must contain at least one epitope (i.e., the specific biochemical unit capable of causing an immune response).

As used herein, the terms "home testing" and "point of care testing" refer to testing that occurs outside of a laboratory environment. Such testing can occur indoors or outdoors at, for example, a private residence, a place of business, public or private land, in a vehicle, as well as at the patient's bedside.

As used herein, the term "virus" refers to minute infectious agents, which with certain exceptions, are not observable by light microscopy, lack independent metabolism, and are able to replicate only within a living host cell. The individual particles (i.e., virions) consist of nucleic acid and a protein shell or coat; some virions also have a lipid containing membrane. The term "virus" encompasses all types of viruses, including animal, plant, phage, and other viruses.

As used herein, term "nanostructures" refers to microscopic structures, typically measured on a nanometer scale. Such structures include various three-dimensional assemblies, including, but not limited to, liposomes, films, multilayers, braided, lamellar, helical, tubular, and fiber-like shapes, and combinations thereof. Such structures can, in some embodiments, exist as solvated polymers in aggregate forms such as rods and coils. Such structures can also be formed from inorganic materials, such as prepared by the physical deposition of a gold film onto the surface of a solid, proteins immobilized on surfaces that have been mechanically rubbed, and polymeric materials that have been molded or imprinted with topography by using a silicon template prepared by electron beam lithography.

As used herein, the terms "self-assembling monomers" and "lipid monomers" refer to molecules that spontaneously associate to form molecular assemblies. In one sense, this can refer to surfactant molecules that associate to form surfactant molecular assemblies. The term "self-assembling monomers" includes single molecules (e.g., a single lipid molecule) and small molecular assemblies (e.g., polymerized lipids), whereby the individual small molecular assemblies can be further aggregated (e.g., assembled and polymerized) into larger molecular assemblies.

As used herein, the term "linker" or "spacer molecule" refers to material that links one entity to another. In one sense, a molecule or molecular group can be a linker that is covalent attached two or more other molecules (e.g., linking a ligand to a self-assembling monomer).

As used herein, the term "bond" refers to the linkage between atoms in molecules and between ions and molecules in crystals. The term "single bond" refers to a bond with two electrons occupying the bonding orbital. Single bonds between atoms in molecular notations are represented by a single line drawn between two atoms (e.g., C—C). The term "double bond" refers to a bond that shares two electron pairs. Double bonds are stronger than single bonds and are more reactive. The term "triple bond" refers to the sharing of three electron pairs. As used herein, the term "ene-yne" refers to alternating double and triple bonds. As used herein the terms "amine bond," "thiol bond," and "aldehyde bond" refer to any bond formed between an amine group (i.e., a chemical group derived from ammonia by replacement of one or more of its hydrogen atoms by hydrocarbon groups), a thiol group (i.e., sulfur analogs of alcohols), and an aldehyde group (i.e., the chemical group —CHO joined directly onto another carbon atom), respectively, and another atom or molecule.

As used herein, the term "covalent bond" refers to the linkage of two atoms by the sharing of two electrons, one contributed by each of the atoms.

As used herein, the term "spectrum" refers to the distribution of light energies arranged in order of wavelength.

As used the term "visible spectrum" refers to light radiation that contains wavelengths from approximately 360 nm to approximately 800 nm.

As used herein, the term "substrate" refers to a solid object or surface upon which another material is layered or attached such as mesogens. Solid supports include, but are not limited to, glass, metals, gels, and filter paper, among others.

As used herein, the terms "array" and "patterned array" refer to an arrangement of elements (i.e., entities) into a material or device. For example, combining several types of ligand binding molecules (e.g., antibodies or nucleic acids) into an analyte-detecting device, would constitute an array.

As used herein, the term "in situ" refers to processes, events, objects, or information that are present or take place within the context of their natural environment.

As used herein, the term "sample" is used in its broadest sense. In one sense it can refer to a biopolymeric material. In another sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, crystals and industrial samples. These examples are not to be construed as limiting the sample types applicable to the present invention.

As used herein, the term "liquid crystal" refers to a thermodynamic stable phase characterized by anisotropy of properties without the existence of a three-dimensional crystal lattice, preferably lying in the temperature range between the solid and isotropic liquid phase.

As used herein, the term "mesogen" refers to compound(s) that form liquid crystals, and in particular rigid rodlike or disclike molecules that are components of liquid crystalline materials.

As used herein, "thermotropic liquid crystal" refers to liquid crystals that result from the melting of mesogenic solids due to an increase in temperature. Both pure substances and mixtures form thermotropic liquid crystals.

"Lyotropic," as used herein, refers to molecules that form phases with orientational and/or positional order in a solvent. Lyotropic liquid crystals can be formed using amphiphilic molecules (e.g., sodium laurate, phosphatidylethanolamine, lecithin). The solvent can be water.

As used herein, the term "heterogenous surface" refers to a surface that orients liquid crystals in at least two separate planes or directions, such as across a gradient.

As used herein, "nematic" refers to liquid crystals in which the long axes of the molecules remain substantially parallel, but the positions of the centers of mass are randomly distributed. Nematic liquid crystals can be substantially oriented by a nearby surface.

"Chiral nematic," as used herein refers to liquid crystals in which the mesogens are optically active. Instead of the director being held locally constant as is the case for nematics, the director rotates in a helical fashion throughout the sample. Chiral nematic crystals show a strong optical activity that is much higher than can be explained on the bases of the rotatory power of the individual mesogens. When light equal in wavelength to the pitch of the director impinges on the liquid crystal, the director acts like a diffraction grating, reflecting most and sometimes all of the light incident on it. If white light is incident on such a material, only one color of light is reflected and it is circularly polarized. This phenomenon is known as selective reflection and is responsible for the iridescent colors produced by chiral nematic crystals.

"Smectic," as used herein refers to liquid crystals which are distinguished from "nematics" by the presence of a greater degree of positional order in addition to orientational order; the molecules spend more time in planes and layers than they do between these planes and layers. "Polar smectic" layers occur when the mesogens have permanent dipole moments. In the smectic A2 phase, for example, successive layers show anti ferroelectric order, with the direction of the permanent dipole alternating from layer to layer. If the molecule contains a permanent dipole moment transverse to the long molecular axis, then the chiral smectic phase is ferroelectric. A device utilizing this phase can be intrinsically bistable.

"Frustrated phases," as used herein, refers to another class of phases formed by chiral molecules. These phases are not chiral, however, twist is introduced into the phase by an array of grain boundaries. A cubic lattice of defects (where the director is not defined) exist in a complicated, orientationally ordered twisted structure. The distance between these defects is hundreds of nanometers, so these phases reflect light just as crystals reflect x-rays.

"Discotic phases" are formed from molecules that are disc shaped rather than elongated. Usually these molecules have aromatic cores and six lateral substituents. If the molecules are chiral or a chiral dopant is added to a discotic liquid crystal, a chiral nematic discotic phase can form. "Viewed between crossed polarizers" means polarizers whose transmission axes are aligned at some angle.

"Polarizer" means a device, which in the transmission of electromagnetic radiation, confines the vibration of the electric and magnetic field vectors of light to substantially one plane.

"Mesogen-aligning substrate" means a substrate that causes certain mesogens to align in a substantially similarly ordered direction in a liquid crystal when in contact with the substrate.

DETAILED DESCRIPTION OF THE INVENTION

The present invention relates to the field of detection of analytes, and in particular to detection of viruses, cells, bacteria, lipid-membrane containing organisms, proteins, nucleic acids, carbohydrates and other biomolecules, organic molecules and inorganic molecules using a liquid crystal assay format. Methods have been developed using liquid crystals that allow for the detection of various target species in samples taken from sources such as the environment or a living organism. Detection of a target species is often necessary in clinical situations before a prescribed method of treatment may be undertaken and an illness diagnosed.

The distinguishing characteristic of a liquid crystalline state is the tendency of the molecules (mesogens) to orientate along a common axis, called the director. This is in contrast to molecules in the liquid phase, which have no intrinsic order. In the solid state, molecules are highly ordered and have little translational freedom. Liquid crystals often have two indices of refraction because light polarized parallel to the director has a different index of refraction then light polarized perpendicular to the director (i.e., the light polarized parallel to the director travels at a different velocity than light polarized perpendicular to the director). Light traveling through a birefringent material is often characterized by a fast component (i.e., the ordinary ray) and a slow component (i.e., the extraordinary ray). Because the two components travel at different velocities, the waves get out of phase. When the rays are recombined as they exit the birefringent material, the polarization state has changed because of this phase difference. The birefringence of a material is characterized by the difference in the indices of refraction for the ordinary and extraordinary rays Ordinary white light is made up of waves that fluctuate at all possible angles. Light is considered to be "linearly polarized" when it contains waves that substantially fluctuate in one specific plane. A polarizer is a material that allows primarily light with a specific angle of vibration to pass through. The direction of fluctuation passed by the polarizer is called the "easy" axis. If two polarizers are set up in series so that their optical axes are parallel, light passes through both. However, if the axes are set up 90 degrees apart (or crossed), the polarized light from the first is extinguished by the second. As the angle rotates from 0 to 90 degrees, the amount of light that is transmitted decreases.

Light can be represented as a transverse electromagnetic wave made up of mutually perpendicular, fluctuating electric and magnetic fields. When a liquid crystal sample is placed between crossed polarizers whose transmission axes are aligned at some angle between the fast and slow direction of the material, incoming linearly polarized light becomes elliptically polarized because of the birefringent nature of the sample. When the elliptically polarized light ray reaches the second polarizer, there is now a component that can pass through the second polarizer, and the region appears bright. The existence of a bright region when light is shined between crossed polarizers indicates the presence of birefringent material such as a liquid crystal. In some liquid crystals, the birefringence is not constant over the entire sample surface because the mesogens manifest a perpendicular alignment while others manifest a planar alignment; therefore, some of the surface areas may appear light and others appear dark when viewed between crossed polarizers depending on how the alignment of the mesogens effects birefringence.

If mesogenic materials are confined between spaced plates with rubbed surfaces and oriented with rubbing directions parallel, the entire liquid crystal sample can be oriented in a planar texture. Mesogens can also be oriented normal to a surface with the use of appropriate polymer films, or in the presence of an electric field applied normal to the surface, giving rise to the homeotropic texture. Mesogens may transition between planar and homeotropic textures, or between different liquid crystal states or between different phase states, such as from a solid to a liquid crystal to a liquid.

In some embodiments, novel liquid crystals are prepared by chemically coupling compounds which possess liquid crystal properties with compounds possessing recognition moieties. The coupled products possess liquid crystal properties while maintaining the capability of the original recognition moiety to recognize and react with target compounds. In further embodiments, the liquid crystals are mesogens that are created by introducing fusion domains into binding receptors via recombinant DNA techniques. Modified proteins, nucleic acids, lipids, and their assemblies are constructed so as to form liquid crystals. Concentrated protein solutions exhibit liquid crystallinity. Using recombinant DNA technology, binding domains are engineered into proteins known to form liquid crystals.

In some embodiments, liquid crystal alignment is amplified by creating elongated structures. In further embodiments, dissolving a protein into a liquid crystal and then polymerizing it with itself or a passive species increases the strength of coupling between a protein binding event and a liquid crystal. The cross linked aggregate will assume a morphology that is coupled to and consistent with the structure of the liquid crystal. This large, oriented structure increases the strength of coupling between the liquid crystal and the bound protein.

Accordingly, the present invention provides improved substrates and devices for the detection of analytes. For convenience, the description of the present invention is divided into the following sections: I. Recognition Moieties; II. Substrates; III. Functionalization of Substrates; IV. Mesogens; V. Direct Detection of Entities with Lipid Membranes; VI. Nonspecific Detection Following Specific Capture; VII. Detection with Lipid Tags; VIII. Kits; IX. Polymer and Protein Liquid Crystals; and X. Pesticide Detection.

I. Recognition Moieties

A variety of recognition moieties find use in the present invention. In preferred embodiments, the recognition moieties are immobilized on detection regions of the substrate (described in more detail below). In some embodiments, the recognition moieties are chemically attached to mesogenic compounds (described in more detail below). In other embodiments of the present invention, a "recognition moiety" attached to or associated with the substrate is utilized to bind to or otherwise interact with another molecule or molecules (e.g., analytes). For example, in some embodiments, recognition moieties are attached to either co-functionalized spacer arms or co-functionalized SAM components which are in turn attached to or associated with the substrate. Furthermore, a recognition moiety can be presented by a polymer surface (e.g., a rubbed polymer surface).

In some preferred embodiments, the recognition moiety comprises an organic functional group. In presently preferred embodiments, the organic functional group is a member selected from the group consisting of amines, carboxylic acids, drugs, chelating agents, crown ethers, cyclodextrins or a combination thereof. In another preferred embodiment, the recognition moiety is a biomolecule. In still further preferred embodiments, the biomolecule is a protein, antigen binding protein, peptide, nucleic acid (e.g., single nucleotides or nucleosides, oligonucleotides, polynucleotides and single- and higher-stranded nucleic acids) or a combination thereof. In a presently preferred embodiment, the recognition moiety is biotin. In some embodiments, the recognition moieties are antigen binding proteins. Examples of antigen binding proteins finding use in the present invention include, but are not limited to, immunoglobulins, single chain antibodies, chimeric antibodies, polyclonal antibodies, monoclonal antibodies, and F(ab')2, Fab' and Fab fragments.

Various procedures known in the art may be used for the production of polyclonal antibodies. For the production of antibody, various host animals, including but not limited to rabbits, mice, rats, sheep, goats, etc., can be immunized by injection with the peptide corresponding to an epitope. In a preferred embodiment, the peptide is conjugated to an immunogenic carrier (e.g., diphtheria toxoid, bovine serum albumin (BSA), or keyhole limpet hemocyanin (KLH)). Various adjuvants may be used to increase the immunological response, depending on the host species, including but not limited to Freund's (complete and incomplete), mineral gels (e.g., aluminum hydroxide), surface active substances (e.g., lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum*).

For preparation of monoclonal antibodies, it is contemplated that any technique that provides for the production of antibody molecules by continuous cell lines in culture will find use with the present invention (See e.g., Harlow and Lane, *Antibodies: A Laboratory Manual*, Cold Spring Harbor Laboratory Press, Cold Spring Harbor, N.Y.). These include but are not limited to the hybridoma technique originally developed by Köhler and Milstein (Köhler and Milstein, Nature 256:495-497 [1975]), as well as the trioma technique, the human B-cell hybridoma technique (See e.g., Kozbor et al., Immunol. Tod., 4:72 [1983]), and the EBV-hybridoma technique to produce human monoclonal antibodies (Cole et al., in *Monoclonal Antibodies and Cancer Therapy*, Alan R. Liss, Inc., pp. 77-96 [1985]).

In addition, it is contemplated that techniques described for the production of single chain antibodies (U.S. Pat. No. 4,946,778; herein incorporated by reference) will find use in producing specific single chain antibodies that serve as recognition moieties. Furthermore, it is contemplated that any technique suitable for producing antibody fragments will find use in generating antibody fragments that are useful recognition moieties. For example, such fragments include but are not limited to: F(ab')2 fragment that can be produced by pepsin digestion of the antibody molecule; Fab' fragments that can be generated by reducing the disulfide bridges of the F(ab')2 fragment, and Fab fragments that can be generated by treating the antibody molecule with papain and a reducing agent. In still further embodiments, the recognition moiety comprises a phage displaying an antigen binding protein.

When the recognition moiety is an amine, in preferred embodiments, the recognition moiety will interact with a structure on the analyte which reacts by binding to the amine (e.g., carbonyl groups, alkylhalo groups). In another preferred embodiment, the amine is protonated by an acidic moiety on the analyte of interest (e.g., carboxylic acid, sulfonic acid).

In certain preferred embodiments, when the recognition moiety is a carboxylic acid, the recognition moiety will interact with the analyte by complexation (e.g., metal ions). In still other preferred embodiments, the carboxylic acid will protonate a basic group on the analyte (e.g. amine).

In another preferred embodiment, the recognition moiety is a drug moiety. The drug moieties can be agents already accepted for clinical use or they can be drugs whose use is experimental, or whose activity or mechanism of action is under investigation. The drug moieties can have a proven action in a given disease state or can be only hypothesized to show desirable action in a given disease state. In a preferred embodiment, the drug moieties are compounds that are being screened for their ability to interact with an analyte of choice. As such, drug moieties that are useful in practicing the instant invention include drugs from a broad range of drug classes having a variety of pharmacological activities.

Classes of useful agents include, for example, non-steroidal anti-inflammatory drugs (NSAIDS). The MAIDS can, for example, be selected from the following categories: (e.g., propionic acid derivatives, acetic acid derivatives, fenamic acid derivatives, biphenylcarboxylic acid derivatives and oxicams); steroidal anti-inflammatory drugs including hydrocortisone and the like; antihistaminic drugs (e.g., chlorpheniranune, triprolidine); antitussive drugs (e.g., dextromethorphan, codeine, carmiphen and carbetapentane); antipruritic drugs (e.g., methidilizine and trimeprizine); anticholinergic drugs (e.g., scopolamine, atropine, homatropine, levodopa); anti-emetic and antinauseant drugs (e.g., cyclizine, meclizine, chlorpromazine, buclizine); anorexic drugs (e.g., benzphetamine, phentermine, chlorphenterrnine, fenfluramine); central stimulant drugs (e.g., amphetamine, methamphetamine, dextroamphetamine and methylphenidate); antiarrhythmic drugs (e.g., propanolol, procainamide, disopyraminde, quinidine, encainide); P-adrenergic blocker drugs (e.g., metoprolol, acebutolol, betaxolol, labetalol and timolol); cardiotonic drugs (e.g., milrinone, amrinone and dobutamine); antihypertensive drugs (e.g., enalapril, clonidine, hydralazine, minoxidil, guanadrel, guanethidine); diuretic drugs (e.g., amiloride and hydrochlorothiazide); vasodilator drugs (e.g., diltazem, amiodarone, isosuprine, nylidrin, tolazoline and verapamil); vasoconstrictor drugs (e.g., dihydroergotamine, ergotamine and methylsergide); antiulcer drugs (e.g., ranitidine and cimetidine); anesthetic drugs (e.g., lidocaine, bupivacaine, chlorprocaine, dibucaine); antidepressant drugs (e.g., imipramine, desipramine, amitryptiline, nortryptiline); tranquilizer and sedative drugs (e.g., chlordiazepoxide, benacytyzine, benzquinamide, flurazapam, hydroxyzine, loxapine and promazine); antipsychotic drugs (e.g., chlorprothixene, fluphenazine, haloperidol, molindone, thioridazine and trifluoperazine); antimicrobial drugs (antibacterial, antifungal, antiprotozoal and antiviral drugs).

Antimicrobial drugs which are preferred for incorporation into the present composition include, for example, pharmaceutically acceptable salts of β-lactam drugs, quinolone drugs, ciprofloxacin, norfloxacin, tetracycline, erythromycin, amikacin, triclosan, doxycycline, capreomycin, chlorhexidine, chlortetracycline, oxytetracycline, clindamycin, ethambutol, hexamidine isothionate, metronidazole; pentamidine, gentamycin, kanamycin, lineomycin, methacycline, methenamine, minocycline, neomycin, netilmycin, paromomycin, streptomycin, tobramycin, miconazole, and amanfadine.

Other drug moieties of use in practicing the present invention include antineoplastic drugs (e.g., antiandrogens (e.g., leuprolide or flutamide), cytocidal agents (e.g., adriamycin, doxorubicin, taxol, cyclophosphamide, busulfan, cisplatin, a-2-interferon) anti-estrogens (e.g., tamoxifen), antimetabolites (e.g., fluorouracil, methotrexate, mercaptopurine, thioguanine).

The recognition moiety can also comprise hormones (e.g., medroxyprogesterone, estradiol, leuprolide, megestrol, octreotide or somatostatin); muscle relaxant drugs (e.g., cinnamedrine, cyclobenzaprine, flavoxate, orphenadrine, papaverine, mebeverine, idaverine, ritodrine, dephenoxylate, dantrolene and azumolen); antispasmodic drugs; bone-active drugs (e.g., diphosphonate and phosphonoalkylphosphinate drug compounds); endocrine modulating drugs (e.g., contraceptives (e.g., ethinodiol, ethinyl estradiol, norethindrone, mestranol, desogestrel, medroxyprogesterone), modulators of diabetes (e.g., glyburide or chlorpropamide), anabolics, such as testolactone or stanozolol, androgens (e.g., methyltestosterone, testosterone or fluoxymesterone), antidiuretics (e.g., desmopressin) and calcitonins).

Also of use in the present invention are estrogens (e.g., diethylstilbesterol), glucocorticoids (e.g., triamcinolone, betamethasone, etc.) and progestogens, such as norethindrone, ethynodiol, norethindrone, levonorgestrel; thyroid agents (e.g., liothyronine or levothyroxine) or anti-thyroid agents (e.g., methimazole); antihyperprolactinemic drugs (e.g., cabergoline); hormone suppressors (e.g., danazol or goserelin), oxytocics (e.g., methylergonovine or oxytocin) and prostaglandins, such as mioprostol, alprostadil or dinoprostone, can also be employed.

Other useful recognition moieties include immunomodulating drugs (e.g., antihistamines, mast cell stabilizers, such as lodoxamide and/or cromolyn, steroids (e.g., triamcinolone, beclomethazone, cortisone, dexamethasone, prednisolone, methylprednisolone, beclomethasone, or clobetasol), histamine $H_2$ antagonists (e.g., famotidine, cimetidine, ranitidine), immunosuppressants (e.g., azathioprine, cyclosporin), etc. Groups with anti-inflammatory activity, such as sulindac, etodolac, ketoprofen and ketorolac, are also of use. Other drugs of use in conjunction with the present invention will be apparent to those of skill in the art.

When the recognition moiety is a chelating agent, crown ether or cyclodextrin, host-guest chemistry will dominate the interaction between the recognition moiety and the analyte. The use of host-guest chemistry allows a great degree of recognition-moiety-analyte specificity to be engineered into a device of the invention. The use of these compounds to bind to specific compounds is well known to those of skill in the art. See, for example, Pitt et al. "The Design of Chelating Agents for the Treatment of Iron Overload," In, INORGANIC CHEMISTRY IN BIOLOGY AND MEDICINE; Martell, A. E., Ed.; American Chemical Society, Washington, D.C., 1980, pp. 279-312; Lindoy, L. F., THE CHEMISTRY OF MACROCYCLIC LIGAND COMPLEXES; Cambridge University Press, Cambridge, 1989; Dugas, H., BIOORGANIC CHEMISTRY; Springer-Verlag, New York, 1989, and references contained therein.

Additionally, many routes allowing the attachment of chelating agents, crown ethers and cyclodextrins to other molecules is available to those of skill in the art. See, for example, Meares et al., "Properties of In Vivo Chelate-Tagged Proteins and Polypeptides." In, MODIFICATION OF PROTEINS: FOOD, NUTRITIONAL, AND PHARMACOLOGICAL ASPECTS;" Feeney, R. E., Whitaker, l. R., Eds., American Chemical Society, Washington, D.C., 1982, pp. 370-387; Kasina et al. *Bioconjugate Chem.* 9:108-117 (1998); Song et al., *Bioconjugate Chem.* 8:249-255 (1997).

In a presently preferred embodiment, the recognition moiety is a polyaminocarboxylate chelating agent such as ethylenediaminetetraacetic acid (EDTA) or diethylenetriaminepentaacetic acid (DTPA). These recognition moieties can be attached to any amine-terminated component of a SAM or a spacer arm, for example, by utilizing the commercially available dianhydride (Aldrich Chemical Co., Milwaukee, Wis.).

In still further preferred embodiments, the recognition moiety is a biomolecule such as a protein, nucleic acid, peptide or an antibody. Biomolecules useful in practicing the present invention can be derived from any source. The biomolecules can be isolated from natural sources or can be produced by synthetic methods. Proteins can be natural proteins or mutated proteins. Mutations can be effected by chemical mutagenesis, site-directed mutagenesis or other means of inducing mutations known to those of skill in the art. Proteins useful in practicing the instant invention include, for example, enzymes, antigens, antibodies and receptors. Antibodies can be either polyclonal or monoclonal. Peptides and nucleic acids can be isolated from natural sources or can be wholly or partially synthetic in origin.

In those embodiments wherein the recognition moiety is a protein or antibody, the protein can be tethered to a SAM component or a spacer arm by any reactive peptide residue available on the surface of the protein. In preferred embodiments, the reactive groups are amines or carboxylates. In particularly preferred embodiments, the reactive groups are the e-amine groups of lysine residues. Furthermore, these molecules can be adsorbed onto the surface of the substrate or SAM by non-specific interactions (e.g., chemisorption, physisorption).

Recognition moieties that are antibodies can be used to recognize analytes which are proteins, peptides, nucleic acids, saccharides or small molecules such as drugs, herbicides, pesticides, industrial chemicals and agents of war. Methods of raising antibodies for specific molecules are well-known to those of skill in the art. See, U.S. Pat. Nos. 5,147,786; 5,334,528; 5,686,237; 5,573,922; each of which is incorporated herein by reference. Methods for attaching antibodies to surfaces are also art-known (See, Delamarche et al. *Langmuir* 12:1944-1946 (1996)).

Peptides and nucleic acids can be attached to a SAM component or spacer arm. Both naturally-derived and synthetic peptides and nucleic acids are of use in conjunction with the present invention. These molecules can be attached to a SAM component or spacer arm by any available reactive group. For example, peptides can be attached through an amine, carboxyl, sulfhydryl, or hydroxyl group. Such a group can reside at a peptide terminus or at a site internal to the peptide chain. Nucleic acids can be attached through a reactive group on a base (e.g., exocyclic amine) or an available hydroxyl group on a sugar moiety (e.g., 3'- or 5'-hydroxyl). The peptide and nucleic acid chains can be further derivatized at one or more sites to allow for the attachment of appropriate reactive groups onto the chain (See, Chrisey et al. *Nucleic Acids Res.* 24:3031-3039 (1996)).

When the peptide or nucleic acid is a fully or partially synthetic molecule, a reactive group or masked reactive group can be incorporated during the process of the synthesis. Many derivatized monomers appropriate for reactive group incorporation in both peptides and nucleic acids are know to those of skill in the art (See, for example, THE PEPTIDES: ANALYSIS, SYNTHESIS, BIOLOGY, Vol. 2: "Special Methods in Peptide Synthesis," Gross, E. and Melenhofer, J., Eds., Academic Press, New York (1980)). Many useful monomers are commercially available (Bachem, Sigma, etc.). This masked group can then be unmasked following the synthesis, at which time it becomes available for reaction with a SAM component or a spacer arm.

In other preferred embodiments, the peptide is attached directly to the substrate (See, Frey et al. *Anal. Chem.* 68:3187-3193 (1996)). In a particularly preferred embodiment, the peptide is attached to a gold substrate through a sulfhydryl group on a cysteine residue. In another preferred embodiment, the peptide is attached through a thiol to a spacer arm which terminates in, for example, an iodoacetamide, chloroacetamide, benzyl iodide, benzyl bromide, alkyl iodide or alkyl bromide. Similar immobilization techniques are known to those of skill in the art (See, for example, Zull et al. *J. Ind Microbiol.* 13:137-143 (1994)).

In another preferred embodiment, the recognition moiety forms an inclusion complex with the analyte of interest. In a particularly preferred embodiment, the recognition moiety is a cyclodextrin or modified cyclodextrin. Cyclodextrins are a group of cyclic oligosaccharides produced by numerous microorganisms. Cyclodextrins have a ring structure which has a basket-like shape. This shape allows cyclodextrins to include many kinds of molecules into their internal cavity (See, for example, Szejtli, J., CYCLODEXTRINS AND THEIR INCLUSION COMPLEXES; Akademiai Klado, Budapest, 1982; and Bender et al., CYCLODEXTRIN CHEMISTRY, Springer-Verlag, Berlin, 1978). Cyclodextrins are able to form inclusion complexes with an array of organic molecules including, for example, drugs, pesticides, herbicides and agents of war (See, Tenjarla et al., *J. Pharm. Sci.* 87:425-429 (1998); Zughul et al., *Pharm. Dev. Technol.* 3:43-53 (1998); and Albers et al., *Crit. Rev. Ther. Drug Carrier Syst.* 12:311-337 (1995)). Importantly, cyclodextrins are able to discriminate between enantiomers of compounds in their inclusion complexes. Thus, in one preferred embodiment, the invention provides for the detection of a particular enantiomer in a mixture of enantiomers (See, Koppenhoefer et al. *J. Chromatogr. A* 793:153-164 (1998)).

The cyclodextrin recognition moiety can be attached to a SAM component, through a spacer arm or directly to the substrate (See, Yamamoto et al., *J. Phys. Chem. B* 101:6855-6860 (1997)). Methods to attach cyclodextrins to other molecules are well known to those of skill in the chromatographic and pharmaceutical arts (See, Sreenivasan, *Appl. Polym. Sci.* 60:2245-2249 (1996)).

In other embodiments, the recognition moieties can be nucleic acids (e.g., RNA or DNA) or receptors that are specific for a particular entity (e.g., virus). In some embodiments, the nucleic acids are aptamers. The isolation of aptamers is described in U.S. Pat. Nos. 5,475,096; 5,270,163; and 5,475,096; and in PCT publications WO 97/38134, WO 98/33941, and WO 99/07724, all of which are herein incorporated by reference.

In some embodiments, recognition moieties are incorporated to detect a variety of bacteria and pathogens. Such recognition moieties include, but not limited to, sialic acid to detect HIV (Wies et al., Nature 333: 426 [1988]), influenza (White et al., Cell 56: 725 [1989]), chlamydia (Infect. Imm. 57: 2378 [1989]), reovirus, *Streptococcus suis, Salmonella*, Sendai virus, mumps, newcastle, myxovirus, and *Neisseria meningitidis;* 9-OAC sialic acid to detect coronavirus, encephalomyelitis virus, and rotavirus; non-sialic acid glycoproteins to detect cytomegalovirus (Virology 176: 337 [1990]) and measles virus (Virology 172: 386 [1989]); CD4 (Khatzman et al., Nature 312: 763 [1985]), vasoactive intestinal peptide (Sacerdote et al., J. of Neuroscience Research 18: 102 [1987]), and peptide T (Ruff et al., FEBS Letters 211: 17 [1987]) to detect HIV; epidermal growth factor to detect vaccinia (Epstein et al., Nature 318: 663 [1985]); acetylcholine receptor to detect rabies (Lentz et al., Science 215: 182 [1982]); Cd3 complement receptor to detect Epstein-Barr virus (Carel et al., J. Biol. Chem. 265: 12293 [1990]); 0-adrenergic receptor to detect rheovirus (Co et al., Proc. Natl. Acad. Sci. 82: 1494 [1985]); ICAM-1 (Marlin et al., Nature 344: 70 [1990]), N-CAM, and myelin-associated glycoprotein MAb (Shephey et al., Proc. Natl. Acad. Sci. 85: 7743 [1988]) to detect rhinovirus; polio virus receptor to detect polio virus (Mendelsohn et al., Cell 56: 855 [1989]); fibroblast growth factor receptor to detect herpesvirus (Kaner et al., Science 248: 1410 [1990]); oligomannose to detect *Escherichia coli*; ganglioside $G_{M}1$ to detect *Neisseria meningitidis*; and antibodies to detect a broad variety of pathogens (e.g., *Neisseria gonorrhoeae, V. vulnificus, V. parahaemolyticus, V. cholerae, V. alginolyticus*, etc.).

In still further embodiments, the recognition moiety is a ligand that interacts with a binding partner. Examples of ligands include, but are not limited to, small organic molecules such as steroid molecules and small drug molecules, proteins, polypeptides and peptides, metal ions, and nucleic acids. In some embodiments, the ligand is recognized by a binding molecule in a sample. Examples of binding molecules include, but are not limited to, steroids, hormones, proteins, polypeptides, and peptides such immunoglobulin molecules and fragments thereof, nucleic acids, and other organic or non-organic molecules. In some preferred embodiments, the ligand is recognized by a binding molecule in a body fluid of a test subject. For example, the ligand can be a virus envelope protein or some other antigenic molecule from a pathogenic organism (such as those listed above). In preferred embodiments, the antigenic molecule (e.g., a protein) is recognized by an antibody molecule in the body fluid of a test subject that has been exposed to the pathogenic organism. In particularly preferred embodiments, the ligand is protein E from the envelope of West Nile Virus.

In some preferred embodiments, the ligands or recognition moieties are complexed with a lipid. The present invention contemplates complexation of the recognition moiety with a variety of lipids and lipid containing materials, including, but not limited to, fatty acids, phospholipids, mono-, di- and tri-glycerides comprising fatty acids and/or phospholipids, lipid bilayers, and liposomes. The lipid containing material can be provided as multilayers, as well as braided, lamellar, helical, tubular, and fiber-like shapes, and combinations thereof. Standard attachment chemistries are available for attaching a recognition moiety or ligand of interest to lipids and lipids containing materials. These attachment chemistries are described in more detail below with reference to liposomes.

II. Mesogens and Coupling with Recognition Moieties

Any compound or mixture of compounds which forms a mesogenic layer can be used in conjunction with the present invention. The mesogens can form thermotropic or lyotropic liquid crystals. Both the thermotropic and lyotropic liquid crystals can exist in a number of forms including nematic, chiral nematic, smectic, polar smectic, chiral smectic, frustrated phases and discotic phases.

TABLE 1

Molecular structure of mesogens suitable for use in Liquid Crystal Assay Devices

| Mesogen | Structure |
| --- | --- |
| Anisaldazine | $CH_3-O-\bigcirc-CH=N-N=CH-\bigcirc-O-CH_3$ |
| NCB | $C_nH_{2n+1}-\bigcirc-\bigcirc-CN$ |
| CBOOA | $C_9H_{19}-O-\bigcirc-N=CH-\bigcirc-CN$ |

TABLE 1-continued

Molecular structure of mesogens suitable for use in Liquid Crystal Assay Devices

| Mesogen | Structure |
|---|---|
| Comp A | $C_7H_{15}$—⬡—⌬—COO—⌬—NCS |
| Comp B | $C_8H_{17}$—O—⌬—O—CO—⌬—O—$CH_2$—⌬—CN |
| $DB_7NO_2$ | $C_7H_{15}$—⌬—O—CO—⌬—O—CO—⌬—$NO_2$ |
| DOBAMBC | $C_{10}H_{21}$—O—⌬—CH=N—⌬—CH=CH—COO—$CH_2$—CH($CH_3$)($C_2H_5$) |
| nOm<br>n = 1, m = 4: MBBA<br>n = 2, m = 4: EBBA | $C_nH_{2n+1}$—O—⌬—CH=N—⌬—$C_mH_{2m+1}$ |
| nOBA<br>n = 8: OOBA<br>n = 9: NOBA | $C_nH_{2n+1}$—O—⌬—COOH |
| nmOBC | $C_nH_{2n+1}$—O—CO—⌬—⌬—O—$C_mH_{2m+1}$ |
| nOCB | $C_nH_{2n+1}$—O—⌬—⌬—CN |
| nOSI | $C_nH_{2n+1}$—O—⌬—⌬—COO—⌬—$CH_2$—CH($CH_3$)($C_2H_5$) |
| 98P | $C_3H_7$—[$CH_2(CH_3)$]$_5$—O—⌬—(pyrimidine)—$C_8H_{17}$ |
| PAA | $CH_3$—O—⌬—N=N(O)—⌬—O—$CH_3$ |
| PYP906 | $C_9H_{19}$—(pyrimidine)—⌬—O—$C_6H_{13}$ |
| $\overline{n}$Sm | $C_nH_{2n+1}$—O—⌬—CO—S—⌬—$C_mH_{2m+1}$ |

Some embodiments of preferred mesogens are displayed in Table 1. In a particularly preferred embodiment, the mesogen is a member selected from the group consisting of 4-cyano-4'-pentylbiphenyl, N-(4methoxybenzylidene)-4-butlyaniline and combinations thereof.

The mesogenic layer can be a substantially pure compound, or it can contain other compounds which enhance or alter characteristics of the mesogen. Thus, in one preferred embodiment, the mesogenic layer further comprises a second compound, for example an alkane, which expands the temperature range over which the nematic and isotropic phases exist. Use of devices having mesogenic layers of this composition allows for detection of the analyte recognition moiety interaction over a greater temperature range.

In some preferred embodiments, the mesogenic layer further comprises a dichroic dye or fluorescent compound. Examples of dichroic dyes and fluorescent compounds useful in the present invention include, but are not limited to, azobenzene, BTBP, polyazo compounds, anthraquinone, perylene dyes, and the like. In particularly preferred embodiments, a dichroic dye of fluorescent compound is selected that complements the orientation dependence of the liquid crystal so that polarized light is not required to read the assay. In some preferred embodiments, if the absorbance of the liquid crystal is in the visible range, then changes in orientation can be observed using ambient light without crossed polarizers. In other preferred embodiments, the dichroic dye or fluorescent compound is used in combination with a fluorimeter and the changes in fluorescence are used to detect changes in orientation of the liquid crystal. DSCG and sunset yellow and other molecules that form chromonic liquid crystals are useful in the present invention.

In some embodiments, the high affinity and specificity of avidin-biotin and antibody-hapten interactions are exploited. Although binding of biotin to native avidin or streptavidin is essentially irreversible, appropriately modified avidins can bind biotinylated probes reversibly, making them valuable reagents for isolating and purifying biotinylated molecules from complex mixtures.

In some preferred embodiments, the mesogens are those compounds having the following formulas:

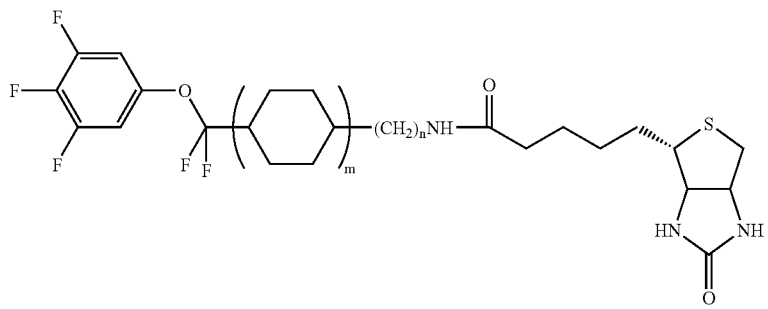

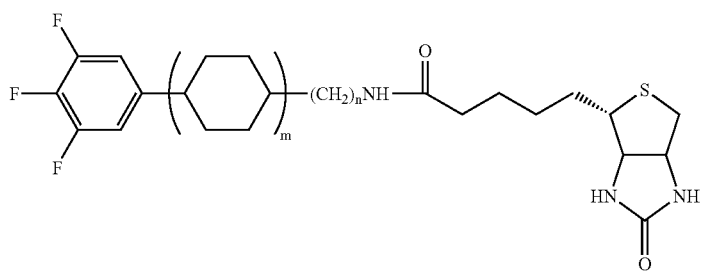

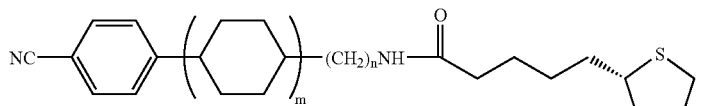

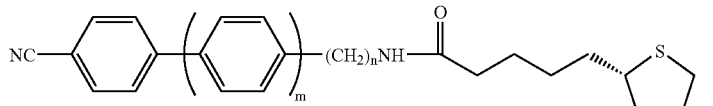

wherein n is 1 to 100, preferably 5 to 12, and m is 1 to 100, preferably 1 to 3. It is appreciated that slight modification in the structure of the disclosed compounds are likely to have similar properties particularly those modifications which include the addition or deletion of a methylene group (e.g. wherein n is 5 or 6) or for the addition of cyclic groups (e.g. wherein m is 1 or 2).

These mesogens can be made using well know methods in the art and those as described herein and as provided in the U.S. publication patent applications listed below, which are hereby incorporated by reference: 20040169159, 20040089843, 20040058158, 20040055529, 20040041125, 20040026661, 20040016905, 20040011996, 20030234384, 20030230737, 20030228426, 20030227000, 20030224125, 20030222245, 20030216554, 20030213935, 20030209691, 20030207047, 20030207046, 20030203129, 20030197154, 20030197153, 20030194511, 20030190436, 20030186002, 20030161971, 20030155552, 20030148043, 20030136945, 20030127629, 20030104143, 20030098443, 20030085377, 20030078447, 20030071244, 20030064172, 20030052306, 20030052305, 20030039769, 20030017279, 20030006399, 20030001137, 20020158227, 20020134967, 20020130300, 2002011926, 220020104983, 20020093004, 20020090469, and 20020084444.

Particularly the transformations of the incorporation of cyclohexane groups can be accomplished by procedures provide for in Zhou and Fu, J. Am. Chem. Soc., 126 (5), 1340-1341, 2004 by using the appropriate derivatives and 4% Ni(cod)$_2$/8% bathophenanthroline/1.6 equiv KOt-Bu in s-BuOH at 60° C.

Figure 2:
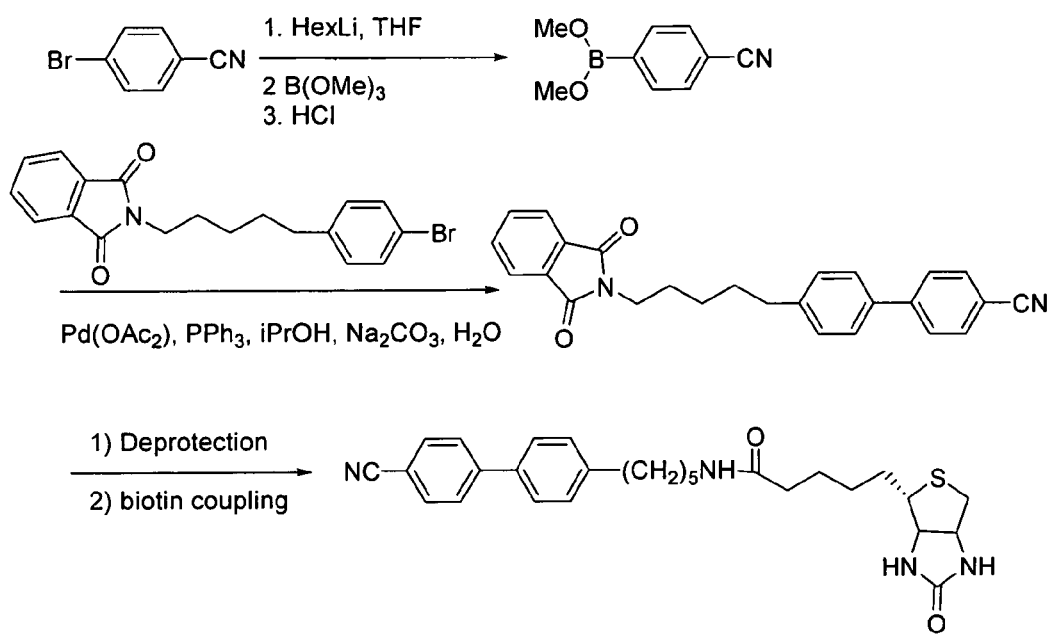
FIG. 2. This is a scheme for the preparation of biotin coupled to a mesogen, 4'-cyanobiphen-4-ylalkyl.

Some of the embodiments include derivatives that can be made using appropriate starting materials. For example p-bromophenylnitrile can be coupled to nitrogen protected alkylated aryls using procedures utilizing boron chemistry known as Suzuki couplings (i.e., the palladium-catalysed cross coupling between organoboronic acid and halides). Potassium trifluoroborates and organoboranes or boronate esters may be used in place of boronic acids (FIG. 2). Exposure of the protected amine allows for coupling of biotin. Preferably this is accomplished by exposure of the free amine to N-(biotinyloxy)succinimide. The protected amine can be obtained using routine lithium-halide coupling procedures and the well-known Gabriel synthesis (i.e., Potassium phthalimide as a NH$_2$-synthon allowing the preparation of primary amines by reaction with alkyl halides). Free amine is exposed by reaction with base or hydrazine.

Chromoglicic acid (i.e., 5,5'-[(2-hydroxy-1,3-propanediyl)bis(oxy)]bis[4-oxo-4H-1-benzopyran-2-carboxylic acid]) is a mesogenic dicarboxylic acid. A recognition moiety can be coupled directly to one of the two carboxylic acid groups using traditional coupling techniques or one of the two carboxylic acids can be esterified with an alcohol (e.g., hexanol) followed by coupling a recognition moiety (FIG. 1). Coupling can be accomplished by creating an N-oxysuccinimide for reaction with an amine group on the protein of interest.

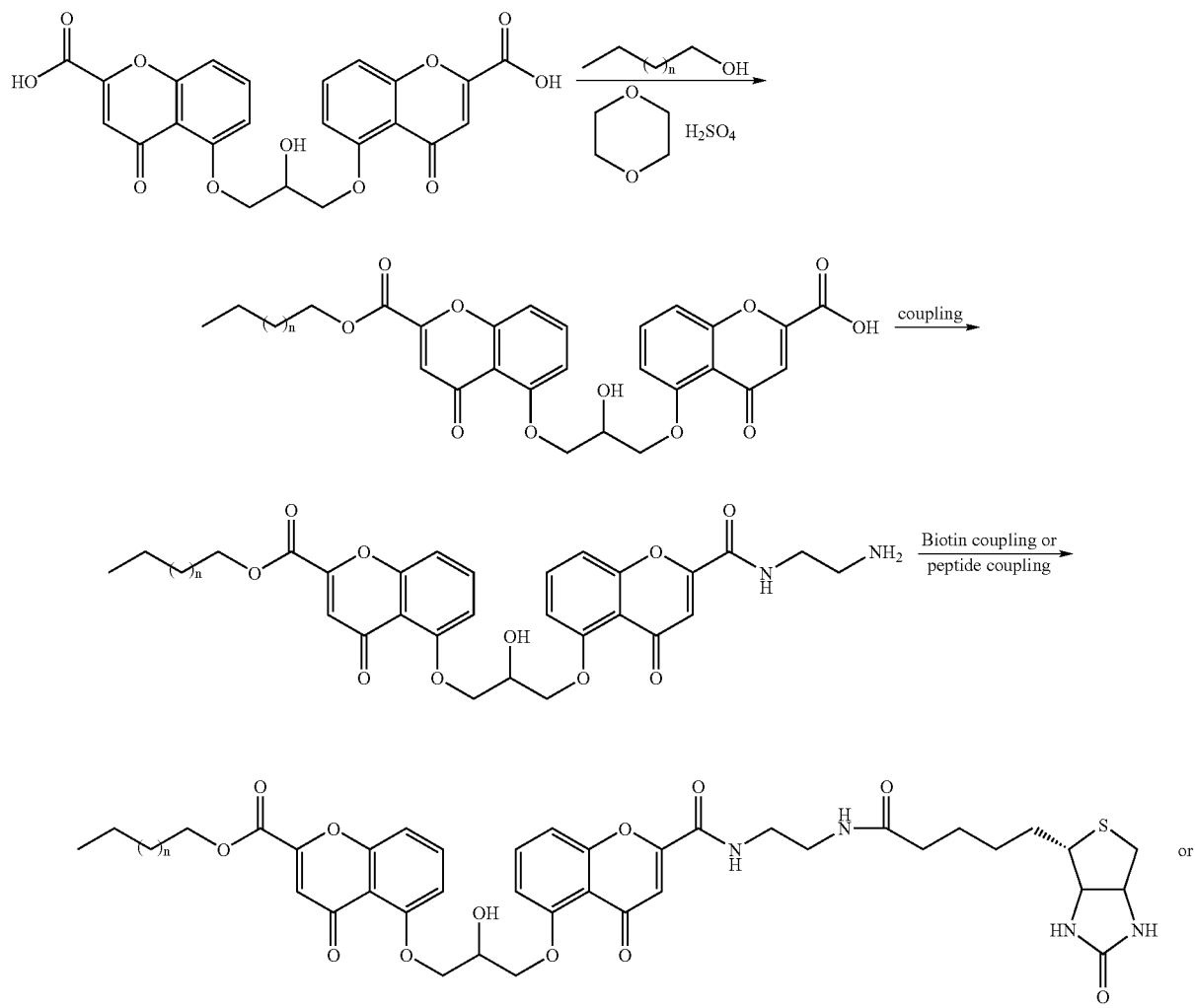

-continued

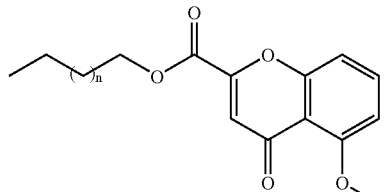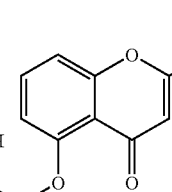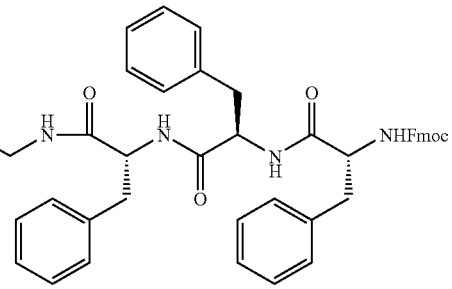

III. Substrates

Substrates that are useful in practicing the present invention (e.g., for constructing the devices of the present invention) can be made of practically any physicochemically stable material. In a preferred embodiment, the substrate material is non-reactive towards the constituents of the mesogenic layer. In some preferred embodiments, the substrates are fabricated or treated so that they are capable of orienting a liquid crystal. In some embodiments, the surface of the substrate is anisotropic. The substrates can be either rigid or flexible and can be either optically transparent or optically opaque. The substrates can be electrical insulators, conductors or semiconductors. Further, the substrates can be substantially impermeable to liquids, vapors and/or gases or, alternatively, the substrates can be permeable to one or more of these classes of materials. Exemplary substrate materials include, but are not limited to, inorganic crystals, inorganic glasses, inorganic oxides, metals, organic polymers and combinations thereof. In some embodiments, the substrates have microchannels therein for the delivery of sample and/or other reagents to the substrate surface or detection regions thereon. The design and use of microchannels are described, for example, in U.S. Pat. Nos. 6,425,972, 6,418,968, 6,447,727, 6,432,720, 5,976,336, 5,882,465, 5,876,675, 6,186,660, 6,100,541, 6,379,974, 6,267,858, 6,251,343, 6,238,538, 6,182,733, 6,068,752, 6,429,025, 6,413,782, 6,274,089, 6,150,180, 6,046,056, 6,358,387, 6,321,791, 6,326,083, 6,171,067, and 6,167,910, all of which are incorporated herein by reference.

A. Inorganic Crystal and Glasses

In some embodiments of the present invention, inorganic crystals and inorganic glasses are utilized as substrate materials (e.g., LiF, NaF, NaCl, KBr, KI, $CaF_2$, $MgF_2$, $HgF_2$, BN, $AsS_3$, ZnS, $Si_3N_4$ and the like). The crystals and glasses can be prepared by art standard techniques (See, e.g., Goodman, C. H. L., Crystal Growth Theory and Techniques, Plenum Press, New York 1974). Alternatively, the crystals can be purchased commercially (e.g., Fischer Scientific). The crystals can be the sole component of the substrate or they can be coated with one or more additional substrate components. Thus, it is within the scope of the present invention to utilize crystals coated with, for example one or more metal films or a metal film and an organic polymer. Additionally, a crystal can constitute a portion of a substrate which contacts another portion of the substrate made of a different material, or a different physical form (e.g., a glass) of the same material. Other useful substrate configurations utilizing inorganic crystals and/or glasses will be apparent to those of skill in the art.

B. Inorganic Oxides

In other embodiments of the present invention, inorganic oxides are utilized as the substrate. Inorganic oxides of use in the present invention include, for example, $Cs_2O$, $Mg(OH)_2$, $TiO_2$, $ZrO_2$, $CeO_2$, $Y_2O_3$, $Cr_2O_3$, $Fe_2O_3$, NiO, ZnO, $Al_2O_3$, $SiO_2$ (glass), quartz, $In_2O_3$, $SnO_2$, $PbO_2$ and the like. The inorganic oxides can be utilized in a variety of physical forms such as films, supported powders, glasses, crystals and the like. A substrate can consist of a single inorganic oxide or a composite of more than one inorganic oxide. For example, a composite of inorganic oxides can have a layered structure (i.e., a second oxide deposited on a first oxide) or two or more oxides can be arranged in a contiguous non-layered structure. In addition, one or more oxides can be admixed as particles of various sizes and deposited on a support such as a glass or metal sheet. Further, a layer of one or more inorganic oxides can be intercalated between two other substrate layers (e.g., metal-oxide-metal, metal-oxide-crystal).

In a presently preferred embodiment, the substrate is a rigid structure that is impermeable to liquids and gases. In this embodiment, the substrate consists of a glass plate onto which a metal, such as gold is layered by evaporative deposition. In a still further preferred embodiment, the substrate is a glass plate ($SiO_2$) onto which a first metal layer such as titanium has been layered. A layer of a second metal such as gold is then layered on top of the first metal layer.

C. Metals

In still further embodiments of the present invention, metals are utilized as substrates. The metal can be used as a crystal, a sheet or a powder. The metal can be deposited onto a backing by any method known to those of skill in the art including, but not limited to, evaporative deposition, sputtering, electroless deposition, electrolytic deposition and adsorption or deposition of preform particles of the metal including metallic nanoparticles.

Any metal that is chemically inert towards the mesogenic layer will be useful as a substrate in the present invention. Metals that are reactive or interactive towards the mesogenic layer will also be useful in the present invention. Metals that are presently preferred as substrates include, but are not limited to, gold, silver, platinum, palladium, nickel and copper. In one embodiment, more than one metal is used. The more than one metal can be present as an alloy or they can be formed into a layered "sandwich" structure, or they can be laterally adjacent to one another. In a preferred embodiment, the metal used for the substrate is gold. In a particularly preferred embodiment the metal used is gold layered on titanium.

The metal layers can be either permeable or impermeable to materials such as liquids, solutions, vapors and gases.

D. Organic Polymers

In still other embodiments of the present invention, organic polymers are utilized as substrate materials. Organic polymers useful as substrates in the present invention include polymers that are permeable to gases, liquids and molecules in solution. Other useful polymers are those that are impermeable to one or more of these same classes of compounds.

Organic polymers that form useful substrates include, for example, polyalkenes (e.g., polyethylene, polyisobutene, polybutadiene), polyacrylics (e.g., polyacrylate, polymethyl methacrylate, polycyanoacrylate), polyvinyls (e.g., polyvinyl alcohol, polyvinyl acetate, polyvinyl butyral, polyvinyl chloride), polystyrenes, polycarbonates, polyesters, polyurethanes, polyamides, polyimides, polysulfone, polysiloxanes, polyheterocycles, cellulose derivative (e.g., methyl cellulose, cellulose acetate, nitrocellulose), polysilanes, fluorinated polymers, epoxies, polyethers and phenolic resins (See, Cognard, J. ALIGNMENT OF NEMATIC LIQUID CRYSTALS AND THEIR MIXTURES, in Mol. Cryst. Liq. Cryst. 1:1-74 (1982)). Presently preferred organic polymers include polydimethylsiloxane, polyethylene, polyacrylonitrile, cellulosic materials, polycarbonates and polyvinyl pyridinium.

In a presently preferred embodiment, the substrate is permeable and it consists of a layer of gold, or gold over titanium, which is deposited on a polymeric membrane, or other material, that is permeable to liquids, vapors and/or gases. The liquids and gases can be pure compounds (e.g., chloroform, carbon monoxide) or they can be compounds which are dispersed in other molecules (e.g., aqueous protein solutions, herbicides in air, alcoholic solutions of small organic molecules). Useful permeable membranes include, but are not limited to, flexible cellulosic materials (e.g., regenerated cellulose dialysis membranes), rigid cellulosic materials (e.g., cellulose ester dialysis membranes), rigid polyvinylidene fluoride membranes, polydimethylsiloxane and track etched polycarbonate membranes.

In a further preferred embodiment, the layer of gold on the permeable membrane is itself permeable. In a still further preferred embodiment, the permeable gold layer has a thickness of about 70 Angstroms or less.

In those embodiments wherein the permeability of the substrate is not a concern and a layer of a metal film is used, the film can be as thick as is necessary for a particular application. For example, if the film is used as an electrode, the film can be thicker than in an embodiment in which it is necessary for the film to be transparent or semi-transparent to light.

Thus, in a preferred embodiment, the film is of a thickness of from about 0.01 nanometer to about 1 micrometer. In a further preferred embodiment, the film is of a thickness of from about 5 nanometers to about 100 nanometers. In yet a further preferred embodiment, the film is of a thickness of from about 10 nanometers to about 50 nanometers.

III. Functionalization of Substrates

In some embodiments, the surface of the substrate is functionalized so that a recognition moiety is immobilized on the surface of the substrate. In some embodiments, the immobilized recognition moiety forms a detection region. In some embodiments, a plurality of detection regions are formed on the surface of the substrate. In some embodiments, the same recognition moiety is provided on two or more of the plurality of detection regions, while in other embodiments, at least two different recognition moieties are immobilized on one or more of the plurality of detection regions. In some embodiments, the recognition moieties are arrayed in discreet detection regions on the substrate surfaces by the methods described in more detail below.

A. Self-Assembled Monolayers

In some embodiments, the surface of the substrate is first functionalized by forming a self-assembled monolayer (SAM) on the substrate surface. Self-assembled monolayers are preferably depicted as an assembly of organized, closely packed linear molecules. There are two widely-used methods to deposit molecular monolayers on solid substrates: Langmuir-Blodgett transfer and self-assembly. Additional methods include techniques such as depositing a vapor of the monolayer precursor onto a substrate surface and the layer-by-layer deposition of polymers and polyelectrolytes from solution (Ladam et al., Protein Adsorption onto Auto-Assembled Polyelectrolyte Films, Langmuir; 2001; 17(3); 878-882).

The composition of a layer of a SAM useful in the present invention can be varied over a wide range of compound structures and molar ratios. In one embodiment, the SAM is formed from only one compound. In a presently preferred embodiment, the SAM is formed from two or more components. In another preferred embodiment, when two or more components are used, one component is a long-chain hydrocarbon having a chain length of between 10 and 25 carbons and a second component is a short-chain hydrocarbon having a chain length of between 1 and 9 carbon atoms. In particularly preferred embodiments, the SAM is formed from $CH_3(CH_2)_{15}SH$ and $CH_3(CH_2)_4SH$ or $CH_3(CH_2)_{15}SH$ and $CH_3(CH_2)_9SH$. In any of the above described embodiments, the carbon chains can be functionalized at the ω-terminus (e.g., $NH_2$, COOH, OH, CN), at internal positions of the chain (e.g., aza, oxa, thia) or at both the ω-terminus and internal positions of the chain.

A recognition moiety can be attached to the surface of a SAM by any of a large number of art-known attachment methods. In one preferred embodiment, a reactive SAM component is attached to the substrate and the recognition moiety is subsequently bound to the SAM component via the reactive group on the component and a group of complementary reactivity on the recognition moiety (See, e.g., Hegner et al. *Biophys. J.* 70:2052-2066 (1996)). In another preferred embodiment, the recognition moiety is attached to the SAM component prior to immobilizing the SAM component on the substrate surface: the recognition moiety-SAM component cassette is then attached to the substrate. In a still further preferred embodiment, the recognition moiety is attached to the substrate via a displacement reaction. In this embodiment, the SAM is preformed and then a fraction of the SAM components are displaced by a recognition moiety or a SAM component bearing a virus recognition moiety. In still other embodiments, the polypeptide recognition moieties are adsorbed directly onto hydrophobic monolayers such as $CH_3(CH_2)_{15}SH$. In embodiments where the recognition moiety is an antibody or other molecule that binds to protein A, protein A is first attached to the monolayer followed by the antibody, which is bound by protein A.

B. Functionalized SAMs

The discussion which follows focuses on the attachment of a reactive SAM component to the substrate surface. This focus is for convenience only and one of skill in the art will understand that the discussion is equally applicable to embodiments in which the SAM component-recognition moiety is preformed prior to its attachment to the substrate. As used herein, "reactive SAM components" refers to components that have a functional group available for reaction with a recognition moiety or other species following the attachment of the component to the substrate.

Currently favored classes of reactions available with reactive SAM components are those that proceed under relatively mild conditions. These include, but are not limited to nucleophilic substitutions (e.g., reactions of amines and alcohols with acyl halides), electrophilic substitutions (e.g., enamine reactions) and additions to carbon-carbon and carbon-heteroatom multiple bonds (e.g., Michael reaction, Diels-Alder addition). These and other useful reactions are discussed in March, ADVANCED ORGANIC CHEMISTRY, Third Ed., John Wiley & Sons, New York, 1985.

According to the present invention, a substrate's surface is functionalized with SAM, components and other species by covalently binding a reactive SAM component to the substrate surface in such a way as to derivatize the substrate surface with a plurality of available reactive functional groups. Reactive groups which can be used in practicing the present invention include, for example, amines, hydroxyl groups, carboxylic acids, carboxylic acid derivatives, alkenes, sulfhydryls, siloxanes, etc.

A wide variety of reaction types are available for the functionalization of a substrate surface. For example, substrates constructed of a plastic such as polypropylene, can be surface derivatized by chromic acid oxidation, and subsequently converted to hydroxylated or aminomethylated surfaces. Substrates made from highly crosslinked divinylbenzene can be surface derivatized by chloromethylation and subsequent functional group manipulation. Additionally, functionalized substrates can be made from etched, reduced polytetrafluoroethylene.

When the substrates are constructed of a siliaceous material such as glass, the surface can be derivatized by reacting the surface Si—OH, SiO—H, and/or Si—Si groups with a functionalizing reagent. When the substrate is made of a metal film, the surface can be derivatized with a material displaying avidity for that metal.

In a preferred embodiment, wherein the substrates are made from glass, the covalent bonding of the reactive group to the glass surface is achieved by conversion of groups on the substrate's surface by a silicon modifying reagent such as:

   (1)

where R is an alkyl group, such as methyl or ethyl, $R^1$ is a linking group between silicon and X and X is a reactive group or a protected reactive group. The reactive group can also be a recognition moiety as discussed below. Silane derivatives having halogens or other leaving groups beside the displayed alkoxy groups are also useful in the present invention.

A number of siloxane functionalizing reagents can be used, for example:
1. Hydroxyalkyl siloxanes (Silylate surface, functionalize with diborane, and $H_2O_2$ to oxidize the alcohol)
   a. allyl trichlorosilane→→3-hydroxypropyl
   b. 7-oct-1-enyl trichlorosilane→→8-hydroxyoctyl
2. Diol(dihydroxyalkyl)siloxanes (silylate surface and hydrolyze to diol)
   a. (glycidyl trimethoxysilane→→(2,3-dihydroxypropyloxy)propyl
3. Aminoalkyl siloxanes (amines requiring no intermediate functionalizing step).
   a. 3-aminopropyl trimethoxysilane→aminopropyl
4. Dimeric secondary aminoalkyl siloxanes
   a. bis(3-trimethoxysilylpropyl)amine→bis(silyloxylpropyl)amine.

It will be apparent to those of skill in the art that an array of similarly useful functionalizing chemistries are available when SAM components other than siloxanes are used. Thus, for example similarly functionalized alkyl thiols can be attached to metal films and subsequently reacted to produce the functional groups such as those exemplified above.

In another preferred embodiment, the substrate is at least partially a metal film, such as a gold film, and the reactive group is tethered to the metal surface by an agent displaying avidity for that surface. In a presently preferred embodiment, the substrate is at least partially a gold film and the group which reacts with the metal surface comprises a thiol, sulfide or disulfide such as:

   (2)

$R^2$ is a linking group between sulfur and $X^2$ and $X^2$ is a reactive group or a protected reactive group. $X^2$ can also be a recognition moiety as discussed below. Y is a member selected from the group consisting of H, $R^3$ and $R^3$—S—, wherein $R^2$ and $R^3$ are independently selected. When $R^2$ and $R^3$ are the same, symmetrical sulfides and disulfides result, and when they are different, asymmetrical sulfides and disulfides result.

A large number of functionalized thiols, sulfides and disulfides are commercially available (Aldrich Chemical Co., St. Louis). Additionally, those of skill in the art have available to them a manifold of synthetic routes with which to produce additional such molecules. For example, amine-functionalized thiols can be produced from the corresponding haloamines, halo-carboxylic acids, etc. by reaction of these halo precursors with sodium sulfhydride. See, e.g., Reid, ORGANIC CHEMISTRY of BIVALENT SULFUR, VOL 1, pp. 21-29, 32-35, vol. 5, pp. 27-34, Chemical Publishing Co., New York, 1.958, 1963. Additionally, functionalized sulfides can be prepared via alkylthio-de-halogenation with a mercaptan salt (See, Reid, ORGANIC CHEMISTRY OF BIVALENT SULFUR, vol. 2, pp. 16-21, 24-29, vol. 3, pp. 11-14, Chemical Publishing Co., New York, 1960). Other methods for producing compounds useful in practicing the present invention will be apparent to those of skill in the art.

In another preferred embodiment, the functionalizing reagent provides for more than one reactive group per each reagent molecule. Using reagents such as Compound 3, below, each reactive site on the substrate surface is, in essence, "amplified" to two or more functional groups:

   (3)

where R is an alkyl group, such as methyl, $R^2$ is a linking group between silicon and $X^2$, $X^2$ is a reactive group or a protected reactive group and n is an integer between 2 and 50, and more preferably between 2 and 20.

Similar amplifying molecules are also of use in those embodiments wherein the substrate is at least partially a metal film. In these embodiments the group which reacts with the metal surface comprises a thiol, sulfide or disulfide such as in Formula (4):

   (4)

As discussed above, $R^2$ is a linking group between sulfur and $X^2$ and $X^2$ is a reactive group or a protected reactive group. $X^2$ can also be a recognition moiety. Y is a member selected from the group consisting of H, $R^3$ and $R^3$—S—, wherein $R^2$ and $R^3$ are independently selected.

R groups of use for $R^1$, $R^2$ and $R^3$ in the above described embodiments of the present invention include, but are not limited to, alkyl, substituted alkyl, aryl, arylalkyl, substituted aryl, substituted arylalkyl, acyl, halogen, hydroxy, amino, alkylamino, acylamino, alkoxy, acyloxy, aryloxy, aryloxyalkyl, mercapto, saturated cyclic hydrocarbon, unsaturated cyclic hydrocarbon, heteroaryl, heteroarylalkyl, substituted heteroaryl, substituted heteroarylalkyl, heterocyclic, substituted heterocyclic and heterocyclicalkyl groups.

In each of Formulae 1-4, above, each of $R^1$, $R^2$ and $R^3$ are either stable or they can be cleaved by chemical or photochemical reactions. For example, R groups comprising ester or disulfide bonds can be cleaved by hydrolysis and reduction, respectively. Also within the scope of the present invention is the use of R groups which are cleaved by light such as, for example, nitrobenzyl derivatives, phenacyl groups, benzoin esters, etc. Other such cleavable groups are well-known to those of skill in the art.

In another preferred embodiment, the organosulfur compound is partially or entirely halogenated. An example of compounds useful in this embodiment include:

$$X^1Q_2C(CQ^1{}_2)_m Z^1 (CQ^2{}_2)_n SH \qquad (5)$$

wherein, $X^1$ is a member selected from the group consisting of H, halogen reactive groups and protected reactive groups. Reactive groups can also be recognition moieties as discussed below. Q, $Q^1$ and $Q^2$ are independently members selected from the group consisting of H and halogen. $Z^1$ is a member selected from the group consisting of —$CQ_2$—, —$CQ^1{}_2$—, —$CQ^2{}_2$—, —O—, —S—, $NR^4$—, —C(O)$NR^4$ and $R^4NC$ (OO—, in which $R^4$ is a member selected from the group consisting of H, alkyl, substituted alkyl, aryl, substituted aryl, heteroaryl and heterocyclic groups and m and n are independently a number between 0 and 40.

In yet another preferred embodiment, the organic layer comprises a compound according to Formula 5 above, in which Q, $Q^1$ and $Q^2$ are independently members selected from the group consisting of H and fluorine. In a still further preferred embodiment, the organic layer comprises compounds having a structure according to Formulae (6) and (7):

$$CF_3(CF_2)_m Z^1 (CH_2)_n SH \qquad (6)$$

$$CF_3(CF_2)_o Z^2 (CH_2)_p SH \qquad (7)$$

wherein, $Z^1$ and $Z^2$ are members independently selected from the group consisting of —$CH_2$—, —O—, —S—, $NR^4$, —C(O)$NR^4$ and $R^4NC(O)$— in which $R^4$ is a member selected from the group consisting of H, alkyl, substituted alkyl, aryl, substituted aryl, heteroaryl and heterocyclic groups. In a presently preferred embodiment, the Z groups of adjacent molecules participate in either an attractive (e.g., hydrogen bonding) or repulsive (e.g., van der Waals) interaction.

In Formula 7, m is a number between 0 and 40, n is a number between 0 and 40, o is a number between 0 and 40 and p is a number between 0 and 40.

In a further preferred embodiment, the compounds of Formulae 6 and 7 are used in conjunction with an organosulfur compound, either halogenated or unhalogenated, that bears a recognition moiety.

When the organic layer is formed from a halogenated organosulfur compound, the organic layer can comprise a single halogenated compound or more than one halogenated compound having different structures. Additionally, these layers can comprise a non-halogenated organosulfur compound.

The reactive functional groups ($X^1$ and $X^2$) are, for example:

(a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters;

(b) hydroxyl groups which can be converted to esters, ethers, aldehydes, etc.

(c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom;

(d) dienophile groups which are capable of participating in Diels-Alder reactions such as, for example, maleimido groups;

(e) aldehyde or ketone groups such that subsequent derivatization is possible via formation of carbonyl derivatives such as, for example, imines, hydrazones, semicarbazones or oximes, or via such mechanisms as Grignard addition or alkyllithium addition;

(f) sulfonyl halide groups for subsequent reaction with amines, for example, to form sulfonamides;

(g) thiol groups which can be converted to disulfides or reacted with acyl halides;

(h) amine or sulfhydryl groups which can be, for example, acylated or alkylated;

(i) alkenes which can undergo, for example, cycloadditions, acylation, Michael addition, etc; and (j) epoxides which can react with, for example, amines and hydroxyl compounds.

The reactive moieties can also be recognition moieties. The nature of these groups is discussed in greater detail below.

The reactive functional groups can be chosen such that they do not participate in, or interfere with, the reaction controlling the attachment of the functionalized SAM component onto the substrate's surface. Alternatively, the reactive functional group can be protected from participating in the reaction by the presence of a protecting group. Those of skill in the art will understand how to protect a particular functional group from interfering with a chosen set of reaction conditions. For examples of useful protecting groups, see Greene et al., PROTECTIVE GROUPS IN ORGANIC SYNTHESIS, John Wiley & Sons, New York, 1991.

In a preferred embodiment, the SAM component bearing the recognition moiety is attached directly and essentially irreversibly via a "stable bond" to the surface of the substrate. A "stable bond", as used herein, is a bond which maintains its chemical integrity over a wide range of conditions (e.g., amide, carbamate, carbon-carbon, ether, etc.). In another preferred embodiment, the SAM component bearing the recognition moiety is attached to the substrate surface by a "cleaveable bond". A "cleaveable bond", as used herein, is a bond that is designed to undergo scission under conditions which do not degrade other bonds in the recognition moiety-analyte complex. Cleaveable bonds include, but are not limited to, disulfide, imine, carbonate and ester bonds.

In certain embodiments, it is advantageous to have the recognition moiety attached to a SAM component having a structure that is different than that of the constituents of the bulk SAM. In this embodiment, the group to which the recognition moiety is bound is referred to as a "spacer arm" or "spacer." Using such spacer arms, the properties of the SAM adjacent to the recognition moiety can be controlled. Properties that are usefully controlled include, for example, hydrophobicity, hydrophilicity, surface-activity and the distance of the recognition moiety from the plane of the substrate and/or the SAM. For example; in a SAM composed of alkanethiols, the recognition moiety can be attached to the substrate or the surface of the SAM via an amine terminated poly(ethyleneglycol). Numerous other combinations of spacer arms and SAMs are accessible to those of skill in the art.

The hydrophilicity of the substrate surface can be enhanced by reaction with polar molecules such as amine-, hydroxyl- and polyhydroxylcontaining molecules. Representative examples include, but are not limited to, polylysine, polyethyleneimine, poly(ethyleneglycol) and poly(propyleneglycol). Suitable functionalization chemistries and strategies for these compounds are known in the art (See, for example, Dunn, R. L., et al., Eds. POLYMERIC DRUGS AND DRUG DELIVERY SYSTEMS, ACS Symposium Series Vol. 469, American Chemical Society, Washington, D.C. 1991).

The hydrophobicity of the substrate surface can be modulated by using a hydrophobic spacer arm such as, for example, long chain diamines, long chain thiols, $\alpha,\omega$-amino acids, etc. Representative hydrophobic spacers include, but are not limited to, 1,6-hexanediamine, 1,8-octanediamine, 6-aminohexanoic acid and 8-aminooctanoic acid.

The substrate surface can also be made surface-active by attaching to the substrate surface a spacer which has surfactant properties. Compounds useful for this purpose include, for example, aminated or hydroxylated detergent molecules such as, for example, 1-aminododecanoic acid.

In another embodiment, the spacer serves to distance the virus recognition moiety from the substrate or SAM. Spacers with this characteristic have several uses. For example, a recognition moiety held too closely to the substrate or SAM surface may not react with incoming analyte, or it may react unacceptably slowly. When an analyte is itself sterically demanding, the reaction leading to recognition moiety-analyte complex formation can be undesirably slowed, or not occur at all, due to the monolithic substrate hindering the approach of the two components.

In another embodiment, the physicochemical characteristics (e.g., hydrophobicity, hydrophilicity, surface activity, conformation) of the substrate surface and/or SAM are altered by attaching a monovalent moiety which is different in composition than the constituents of the bulk SAM and which does not bear a recognition moiety. As used herein, "monovalent moiety" refers to organic molecules with only one reactive functional group. This functional group attaches the molecule to the substrate. "Monovalent moieties" are to be contrasted with the bifunctional "spacer" groups described above. Such monovalent groups are used to modify the hydrophilicity, hydrophobicity, binding characteristics, etc. of the substrate surface. Examples of groups useful for this purpose include long chain alcohols, amines, fatty acids, fatty acid derivatives, poly(ethyleneglycol) monomethyl ethers, etc.

When two or more structurally distinct moieties are used as components of the SAMs, the components can be contacted with the substrate as a mixture of SAM components or, alternatively, the components can be added individually. In those embodiments in which the SAM components are added as a mixture, the mole ratio of a mixture of the components in solution results in the same ratio in the mixed SAM. Depending on the manner in which the SAM is assembled, the two components do not phase segregate into islands (See, Bain and Whitesides, *J. Am. Chem. Soc.* 111:7164 (1989)). This feature of SAMs can be used to immobilize recognition moieties or bulky modifying groups in such a manner that certain interactions, such as steric hindrance, between these molecules is minimized.

The individual components of the SAMs can also be bound to the substrate in a sequential manner. Thus, in one embodiment, a first SAM component is attached to the substrate's surface by "underlabeling" the surface functional groups with less than a stoichiometric equivalent of the first component. The first component can be a SAM component liked to a terminal reactive group or recognition group, a spacer arm or a monovalent moiety. Subsequently, the second component is contacted with the substrate. This second component can either be added in stoichiometric equivalence, stoichiometric excess or can again be used to underlabel to leave sites open for a third component.

In some embodiments amine-terminated surfaces (I) uniformly align liquid crystals and (II) have sufficiently high surface free energy to capture proteins delivered to the surface. A thin gold surface may be exposed to 2-mercaptoethylamine followed by avidin. The high affinity and specificity of avidin-biotin interactions of a biotinylated mesogen is used to orientate the liquid crystal.

C. Polyimides

In some embodiments, the substrates are coated with polyimide layer. It is contemplated that polyimide coated substrates are especially useful because in some instances, the surfaces homeotropically orient a liquid crystal, while in other instances the surfaces can be rubbed to provide an anisotropic surface for orient a liquid crystal. In preferred embodiments, a substrate such as a silicon wafer is coated with a polyimide. In preferred embodiment, the substrate is spin coated with the polyimide. A variety of polyimides find use with the present invention, including, but not limited to Nissan 7210, Nissan 3510, Nissan 410, Nissan 3140, Nissan 5291, and Japan Synthetic Rubber JALS 146-R19 for planar alignment of liquid crystals and Nissan 7511L and SE 1211 for homeotropic orientation of liquid crystals. Surprising, it has been found that the ability of rubbed polyimide surfaces to orient liquid crystals is maintained when a recognition moiety is displayed on the rubbed surface, and then masked when an analyte binds the recognition moiety. Thus, areas where an analyte is bound have a non-ordered liquid crystal and appear white or bright when viewed through cross polars and areas where analyte is not bound remain ordered and appear dark when viewed through cross polars. Surprising, it has also been found that polyimide surfaces that homeotropically orient liquid crystals can be used to report non-specific binding to the surface. In these embodiments, areas where an analyte is bound have a disordered liquid crystal appear white or bright when viewed through cross polars and areas where no analyte is bound maintain the homeotropic orientation and appear dark. These different polyimides provide different anchoring properties and different binding affinity to different proteins which can be used to probe and report the binding events between the proteins. Likewise, different liquid crystals show different response to the specific binding event. Therefore, it is possible to tune the assays by using different liquid crystalline materials such as, 5CB, BL093, TL 216, ZLI 5800, MLC 6613, and (p-methoxybenzylidene)-p-butylaniline (MBBA) with different optical and dielectric properties.

D. Direct Adsorption

In some embodiments, the recognition moiety is immobilized on a substrate by direct adsorption. For example, an antibody can be immobilized onto a thin film of polyurethane spin coated onto a gold substrate surface.

E. Arrays

In some embodiments where the recognition moiety is a polynucleotide or polypeptide, a plurality of recognition moieties are arrayed on the substrates using photo activated chemistry, microcontact printing, and ink-jet printing. In particularly preferred embodiments, photolithography is utilized (See e.g., U.S. Pat. Nos. 6,045,996; 5,925,525; and 5,858,659; each of which is herein incorporated by reference). Using a series of photolithographic masks to define substrate exposure sites, followed by specific chemical synthesis steps, the process constructs high-density arrays of oligonucleotides, with each probe in a predefined position in the array. Multiple probe arrays are synthesized simultaneously on, for example, a large glass wafer. The wafers are then diced, and individual probe arrays are packaged in injection-molded plastic cartridges, which protect them from the environment and serve as chambers for hybridization.

In other embodiments, nucleic acid recognition moieties are electronically captured on a suitable substrate (See e.g., U.S. Pat. Nos. 6,017,696; 6,068,818; and 6,051,380; each of which are herein incorporated by reference). Through the use of microelectronics, this technology enables the active movement and concentration of charged molecules to and from designated test sites on its semiconductor microchip. DNA capture probes unique to a given target are electronically placed at, or "addressed" to, specific sites on the microchip. Since DNA has a strong negative charge, it can be electronically moved to an area of positive charge.

In still further embodiments, ecognition moieties are arrayed on a suitable substrate by utilizing differences in surface tension (See e.g., U.S. Pat. Nos. 6,001,311; 5,985,551; and 5,474,796; each of which is herein incorporated by reference). This technology is based on the fact that fluids can be segregated on a flat surface by differences in surface tension that have been imparted by chemical coatings. Once so segregated, oligonucleotide probes are synthesized directly on the chip by ink-jet printing of reagents. The array with its reaction sites defined by surface tension is mounted on a X/Y translation stage under a set of four piezoelectric nozzles, one for each of the four standard DNA bases. The translation stage moves along each of the rows of the array and the appropriate reagent is delivered to each of the reaction site. For example, the A amidite is delivered only to the sites where amidite A is to be coupled during that synthesis step and so on. Common reagents and washes are delivered by flooding the entire surface and then removing them by spinning.

In still further embodiments, recognition moieties are spotted onto a suitable substrate. Such spotting can be done by hand with a capillary tube or micropipette, or by an automated spotting apparatus such as those available from Affymetrix and Gilson (See e.g., U.S. Pat. Nos. 5,601,980; 6,242,266; 6,040,193; and 5,700,637; each of which is incorporated herein by reference).

F. Blocking

In some embodiments, following immobilization of the recognition moiety on the surface of the substrate, the remainder of the substrate is blocked to guard against non-specific binding to the substrate surface. Examples of suitable blocking agents, include, but are not limited to, serum albumins, zwitterionic polymers, adsorbed lipid layers, dextran and other sugars, cross-linked lipids, polyethylene oxide, polyoxazolines, hydrogels, and milk. In preferred embodiments, the blocking agent bovine serum albumin, human serum albumin or equine serum albumin.

IV. Polymer and Protein Liquid Crystals

Polymer Liquid Crystals (PLCs) are a class of materials that combine the properties of polymers with those of liquid crystals. These "hybrids" show the same mesophases characteristic of ordinary liquid crystals, yet retain many of the useful and versatile properties of polymers. In order for polymers to display liquid crystal characteristics, rod-like or disk-like elements (mesogens) are incorporated into their chains. Main-chain polymer liquid crystals or MC-PLCs are formed when the mesogens are themselves part of the main chain of a polymer. Conversely, side chain polymer liquid crystals or SC-PLCs are formed when the mesogens are connected as side chains to the polymer by a "bridge".

Main chain polymer liquid crystals are formed when rigid elements are incorporated into the backbone of polymers. These rigid regions along the chain allow the polymer to orient into liquid crystals displaying liquid crystal characteristics. Preferably, the mesogenic units are made up of two or more aromatic rings that provide the necessary restriction on movement that allows the polymer to display liquid crystal properties. Decoupling of the mesogens provides for independent movement of the molecules that facilitates proper alignment.

Side chain polymer liquid crystals are formed when mesogenic units are attached to the polymer as side chains. Alignment of the mesogens causes the liquid crystal behavior. In some embodiments, the mesogen is made up of a rigid core of two or more aromatic rings joined together by a functional group. Mesogens, attached as side groups on the backbone of side chain polymer liquid crystals, are able to orient because the spacer allows for independent movement. In preferred embodiments of the current invention, the spacer consists of two to four methylene ($CH_2$) groups attached together in a line. In further preferred embodiments the spacer is a peptide backbone.

In some embodiments of the current invention, the side chain polymer liquid crystals form what is known as the "double comb" configuration. This structure is formed when side chains point away from the backbone in an alternating fashion. The double comb configuration allows the polymers to form layers characteristic of the smectic phase.

Ordinary polymers have not been able to demonstrate the stiffness necessary to compete against traditional materials like steel. It has been observed that polymers with long straight chains are significantly stronger than their tangled counterparts. Main chain liquid crystal polymers are well-suited to ordering processes. For example, the polymer can be oriented in the desired liquid crystal phase and then quenched to create a highly ordered, strong solid with light-weight properties.

Current polymer liquid crystal's demonstrate relatively slow "response times" to electric fields. That is, when a field is applied, the molecules take a long time to align along it. This is undesireable for use in displays where the screen must be able to change rapidly from one view to another. In some embodiments of the current invention polymer liquid crystals demonstrate sufficient response times to electric fields. In further embodiments, a twisted nematic polymer liquid crystal cell is used to make energy efficient displays. A laser is used to selectively melt portions of the display into the liquid crystal phase. The orientation of the cell is then chosen by applying a field across it, just as in an ordinary twisted nematic liquid crystal cell. When the polymer cools down and hardens into a glass, the mesogens will be locked in that configuration and the field can be turned off. In some embodiments, the side chain polymer liquid crystals of the current invention exhibit good properties for applications in optically nonlinear devices including optical waveguides and electro-optic modulators in poled polymeric slab waveguides. In further embodiments, the polymer liquid crystals of the current invention are used as optically-addressed spatial light modulators, tunable notch filters, optical amplifiers, and laser beam deflectors. The properties of ferroelectric chiral smectic C phases make this material useful for films with applications in nonlinear optics.

Some embodiment of the invention, polymer-dispersed liquid crystals (PDLCs) occur. In further embodiment the polymer-dispersed liquid crystals are used in switchable windows and projection displays. PDLCs consist of liquid crystals that are dispersed in a solid polymer matrix. In futher embodiments, changing the orientation of the liquid crystal molecules with an electric field varies the intensity of transmitted light. In further embodiments the polymer-dispersed liquid crystals are prepared in several different ways including: encapsulation (emulsification) and phase separation.

In some embodiments of the invention, a liquid crystal is mixed with a polymer dissolved in water. When the water is evaporated, a layer of polymers surrounds the liquid. Thousands of these tiny "capsules" are produced and distributed through the bulk polymer. In further embodiments, a homogeneous mixture of polymer (or prepolymer) and liquid crystal is first produced. The liquid crystals are then formed by the separation of the two phases. In further embodiments, polymerization-induced phase separation (PIPS) occurs. A liquid crystal is mixed with a solution that has not yet undergone polymerization (a prepolymer). Once a homogeneous solution is formed, the polymerization reaction is initiated. As the reaction progresses, the liquid crystal molecules come out of solution and begin to form droplets. The droplets grow until the polymer binder becomes solid enough that the molecules are trapped and can no longer move easily. In further embodiments Thermally-induced phase separation, or (TIPS) occurs. The polymer binder has a melting temperature below its decomposition temperature. A homogeneous mixture of liquid crystal and a melted polymer is formed. The solution is cooled at a specific rate to induce phase separation. Liquid crystal droplets begin to form as the polymer hardens. The droplets continue to grow until the glass transition temperature of the polymer is crossed. In further embodiments, solvent-induced phased separation, or SIPS, occurs. Both the liquid crystal and polymer are dissolved in a solvent. The solvent is then removed (typically by evaporation) at a controlled rate to begin the phase separation. Droplets start growing as the polymer and liquid crystal come out of solution and stop when all of the solvent has been removed.

In some embodiments of the invention, polymer-dispersed liquid crystals are used in electro-optic applications such as displays and light shutters. In further embodiment the polymer-dispersed liquid crystals are used in electro-optic light shutters in the construction of privacy windows. A thin polymer-dispersed liquid crystal film (about 25 microns thick) is deposited between clear plastic covers. The plastic substrates are coated with a very thin layer of a conducting material such as indium tin oxide (ITO). If the field is OFF, the random array of droplet orientation provides significant differences in indices and hence strong light scattering. In this state, the cell appears opaque. When a voltage is applied, the directors of the individual droplets align with the field. There is now little difference in refractive index for neighboring droplets, and the cell appears transparent.

In some embodiments of the current invention, polymer stabilized liquid crystal cells are prepared. In further embodiments, polymer stabilized liquid crystals are prepared by dissolving and photopolymerizing monomers in a liquid crystals matrix to form a polymer network. For example, a homogeneous alignment is accomplished by pretreatment—coating and rubbing—of the inner side of the bounding glass cell faces. A 3 wt % of a diacrylate monomer (Bis[6-(acryloyloxy)hexyloxy]-1,1'biphenylene) with 0.3 wt % photoinitiator is dissolved in a eutectic mix of several similar low-molar mass liquid crystals. After being sandwiched between the treated glass cell faces, the solution is photopolymerized under an UV light source.

In some embodiments, the invention comprises the use of biological materials to produce liquid crystal products. Expression systems can be used to generate polymer liquid crystals based on amino acid synthesis. Proteins can be purified by expressing the amino acid sequence in a host, such as E. coli. The protein may be expressed in combination with a second amino acid sequence (fusion-proteins) that has properties preferential for purification. For example, The Glutathione S-transferase (GST) gene fusion system is an integrated system for the expression, purification and detection of fusion proteins produced in bacterial, yeast, mammalian and insect cells.

The sequence encoding the GST protein is incorporated into an expression vector, preferably upstream of the multicloning site. The sequence encoding the protein of interest is then cloned into this vector. Induction of the vector results in expression of a fusion protein—the protein of interest fused to the GST protein. The fusion protein can then be released from the cells and purified.

Purification of the fusion protein is facilitated by the affinity of the GST protein for glutathione residues. Glutathione residues are coupled to a resin and the expressed protein product is brought into contact with the resin. The fusion protein will bind to the glutathione-resin complex and all other non-specific proteins can be washed off. The fusion protein can then be released from the resin using a mild elution buffer that is of low pH. Similarly, poly-histidine sequences (his-tags) can be used.

It is possible to remove the GST or his-tag from the protein of interest by using a number of different enzymes (thrombin, factor X), which cleave specific sites between the GST or his-tag and the protein of interest. Fusion proteins can also be detected easily, with a number of antibodies now available on the market.

A relationship exists between the triplet nucleic acid codons of DNA and the chemical nature of amino acids in expressed proteins. A specific interaction between the codons and the amino acids themselves is not made, but instead, the match is made by transfer RNA, that translates the nucleotide language of codons into the amino acid language of proteins. At one end of each tRNA is an anticodon that recognizes the genetic code, and at the other end is the appropriate amino acid for that code.

Transfer RNA molecules are composed of one short chain of RNA, 70-90 nucleotides in length, folded into a trefoil shape. The two ends of the RNA chain are close to one another at a pointed end of an L-shaped structure. The amino acid is added here. The center of the chain forms the rounded leg of the L exposing the three nucleotides that form the anticodon. The amino acid phenylalanine covalently bonds to the tRNA with the anticodon UUU or UUC because these two codons specify the amino acid phenylalanine. The other two loops of the trefoil are bundled into the elbow, where they provide structure to the whole molecule. The four normal RNA bases are adenine, uracil, guanine and cytosine; however, many of the bases are modified to enhance their structures (e.g. in the phenylalanine tRNA, PDB entries 4tna and 6tna). The 5' and 3' ends of the tRNA are base-paired. The amino acid specific for the tRNA is covalently attached to a 3' OH group on the terminal adenine nucleotide referred to as amino acid charging the transfer RNA. Aminoacyl-tRNA synthetases are enzymes that charge the amino acid to each tRNA. Transfer RNAs bring the correct amino acid to the ribosome so that the amino acid can be added to the growing (nascent) polypeptide chain whose sequence is specified by the codons of the mRNA. For example, phenylalanine aminoacyl tRNA synthetase binds a tRNA with the anticodon the amino acid phenylalanine. The enzyme then forms a covalent bond between the carboxyl group of the amino acid and the hydroxyl groups of the pentose sugar of the tRNA. The aminoacyl tRNA synthetase recognizes the specific tRNA because there are specific recognition sites on the tRNA.

In one embodiment, an alternative amino acid recognition is accomplished by selective mutagenesis of the relevant aminoacyl tRNA synthetase to recognize amino acid analogues that are mimics of the cognate amino acid. For instance, an E. coli phenylalanine tRNA synthetase (PheRS) variant carrying a single Ala→Gly amino acid substitution at α-subunit residue 294 (PheRS-αA294G) displays relaxed substrate specificity toward a number of para-substituted phenylalanine mimics. Examples include several halogenated phenylalanines including p-chlorophenylalanine, p-bromophenylalanine and p-iodophenylalanine as well asp-cyanophenylalanine, p-ethynylphenylalanine, p-azidophenylalanine, and 2-, 3-, and 4-pyridylalanine. Introducing an additional mutation, Thr→Gly in position 251 (PheRS-α T251 G/A294G), further enlarges the amino acid binding pocket, which provides space for phenylalanine analogues carrying modifications on the benzene ring and allows activation of still larger unnatural amino acids such as p-acetylphenylalanine. Bentin T., et al., J. Biol. Chem., 279:19, 19839-19845 (2004).

In further embodiments the unnatural amino acids include those of the following formula:

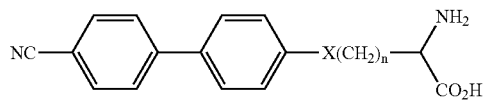

wherein n is 1 to 100, preferably 1 to 10, and more preferably 1, 5, and 8, and X is a bond or O, S, or N, preferably a bond.

The compounds above may be made by methods well known by those skilled in the art or made by the following process starting with 4'-methyl-(1,1'-Biphenyl)-4-carbonitrile:

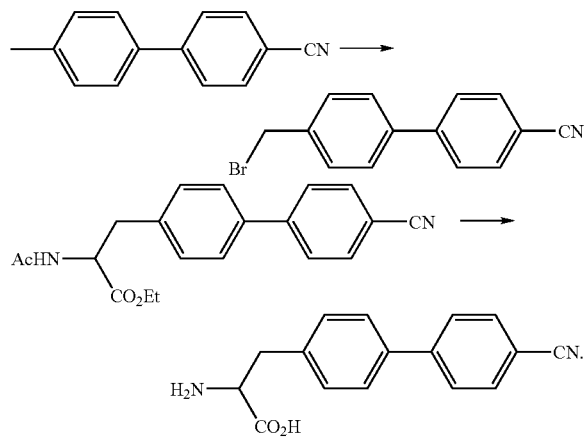

The compounds above may also be made by methods well known by those skilled in the art or made by the following process starting with 4'-hydroxy-(1,1'-Biphenyl)-4-carbonitrile:

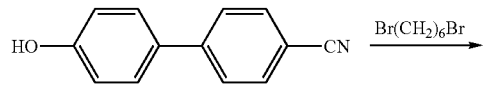

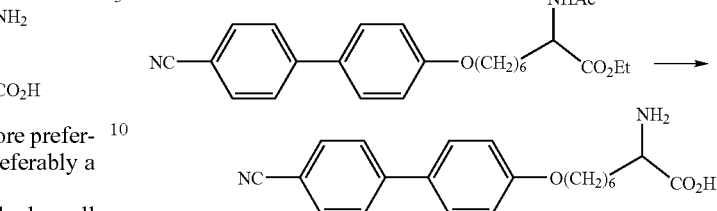

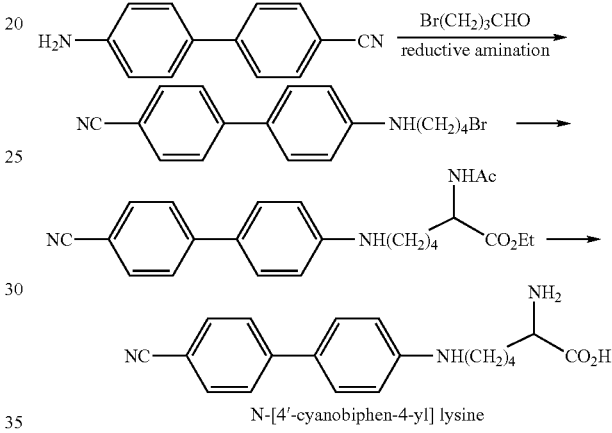

The compounds above may also be made by methods well known by those skilled in the art or made by the following process starting with 4'-amino-(1,1'-Biphenyl)-4-carbonitrile ultimately yielding N-[4'-cyanobiphen-4-yl]lysine:

Any of the synthetic intermediates and products in the schemes may be obtained alternatively by processes previously published or by commercial suppliers including the use of alternative methods well known to those in the art.

In another embodiment of the current invention includes the expression of the liquid crystal amino acid in conjunction with glycine residues in conjunction with a protein recognition moiety.

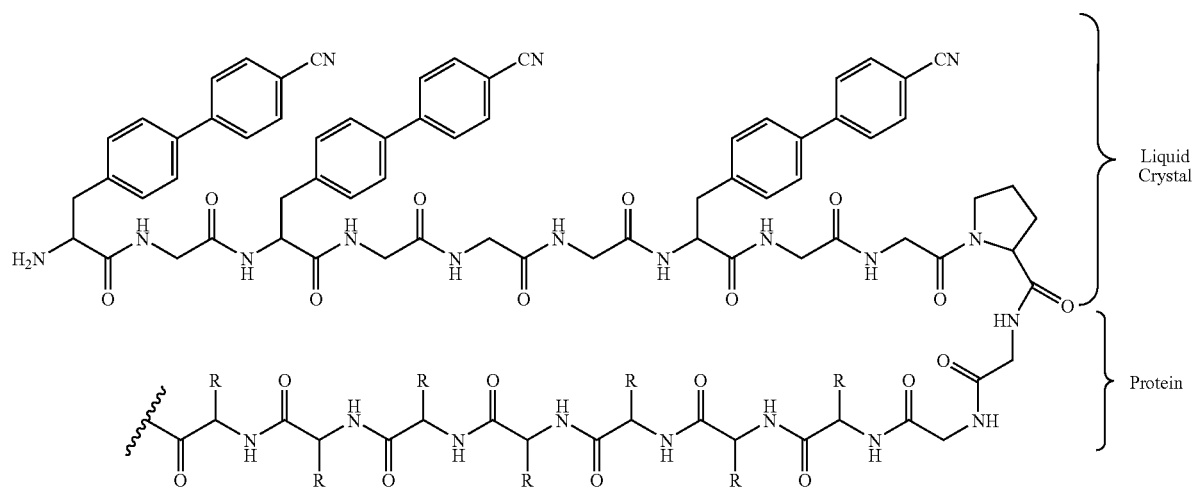

Preferably, the recognition moiety for use in detection can be determine by generating monoclonal antibodies to desire target, sequencing the VH or V light chain regions, and using those sequences to create the recognition moiety.

In Pleau et al., Mol Immunol. 1993 October; 30 (14):1257-64 two monoclonal autoantibodies directed against insulin and peripherin are obtained and the nucleotide sequence of the genes encoding for the V regions of these two antibodies. The protein sequence for anti-insulin monoclonal antibody kappa chain variable region is Seq ID No. 1: QIVLTQSPAI MSASPGEKVT MTCSASSSVS SRYLHWYQQK SEASP-KLWIY GTSNLASGVP ARFSGSGSGT SYSLTVSSVE AEDAATYYCQ QYHSDPYTFG SGTKLEIKR. This protein can be coupled to the liquid crystal sequence and used to create a liquid crystal sensor for insulin (e.g. for use in the diagnosis of a subject with diabetes). The a DNA sequence that expresses the flowing amino acid sequence $[A_a^{LC}(G)_n]_m X(G)_p R$ or portion thereof wherein, $A_a^{LC}$ is any amino acid side chain that forms a liquid crystal, preferably 4'-cyanobiphen-4-ylalanine, G is glycine, and n, m, and p are each separately and individually an integer between 0 and 100, and X is proline or a bond (i.e. no amino acid) and R is a recognition moiety; can be placed in an expression vector having phenylalanine tRNA synthetase (PheRS) variant, for example SEQ. ID. NO. 2: $A_a^{LC}$GGGA$_a^{LC}$ GGGA$_a^{LC}$G GGPGGGGGGG QIVLTQSPAI MSASPGEKVT MTC-SASSSVS SRYLHWYQQK SEASPKLWIY GTSNLAS-GVP ARFSGSGSGT SYSLTVSSVE AEDAATYYCQ QYHSDPYTFG SGTKLEIKR, wherein the letters designated the generally accepted single letter amino acid code except $A_a^{LC}$ is 4'-cyanobiphen-4-ylalanine, can be placed in an expression vector having phenylalanine tRNA synthetase (PheRS) variant capable of alternatively incorporating 4'-cyanobiphen-4-ylalanine. Preferably the phenylalanine tRNA synthetase (PheRS) variant is significantly changes so that it does not continue to incorporate phenylalanine. If the phenylalanine tRNA synthetase (PheRS) variant continues to incorporate phenylalanine, it is preferable that the variable chain sequence does not contain phenylalanine. It is preferably that the variable chain sequence used contains very few phenylalanine amino acid residues and that the few phenylalanine residues present are such that the incorporation of 4'-cyanobiphen-4-ylalanine in the variable sequence does not affect the ability of the recognition moiety to bind the desired analyte. In further embodiments lysine tRNA synthetase (LysRS) variant is capable of incorporating N-[4'-cyanobiphen-4-yl] lysine and N-∈-biotinyl-L-lysine.

In some embodiments, a tRNA synthetase is capable of incorporating N-[4'-cyanobiphen-4-yl]lysine and N-∈-biotinyl-L-lysine; however, the corresponding synthetase has a anticodon not recognized by the tRNA of normal amino acids. For example, in Srinivasan et al., Science 2002 May 24; 296(5572):1459-62, the authors disclose that pyrrolysine is a lysine derivative encoded by the UAG codon in methylamine methyltransferase genes of Methanosarcina barkeri. Near a methyltransferase gene cluster is the pylT gene, which encodes an unusual transfer RNA (tRNA) with a CUA anticodon. The adjacent pylS gene encodes a class II aminoacyl-tRNA synthetase that charges the pylT-derived tRNA with lysine but is not closely related to known lysyl-tRNA synthetases. Charging a tRNA(CUA) with lysine is the first step in translating UAG amber codons as pyrrolysine in certain methanogens. In a further embodiment of the current invention the pylS tRNA synthetase or variant is capable of charging the pylT-derived tRNA with N-[4'-cyanobiphen-4-yl] lysine and/or N-∈-biotinyl-L-lysine. The UAG codon is place in an expression system to produce the desire protein with the N-[4'-cyanobiphen-4-yl]lysine and/or N-∈-biotinyl-L-lysine in the desired location. In Huang et al., Proc Natl Acad Sci USA. 2004 Mar. 2; 101(9): 2706-2711, the authors disclose a number of variable regions for HIV antibodies, which can be used to generate a liquid crystal sensor for use in the diagnosis of HIV.

V. Devices

The present invention also encompasses devices incorporating the components described above. In some preferred embodiments, the devices of the present invention comprise at least one substrate. The at least one substrate comprises a surface that can be contacted with a liquid crystal composition. In some preferred embodiments, the surface of the substrate orients liquid crystals. In some particularly preferred embodiments, the surface is anisotropic. As described in detail above, in some preferred embodiments, the surface is functionalized. In other embodiments, particularly where the liquid crystal composition comprises a recognition moiety, the surface need not be functionalized, but can be functionalized depending upon the application. For example, even in applications where a recognition is not being attached to the substrate, the surface can be functionalized (e.g., with polyimide) in order to provide a surface that is capable orienting liquid crystals (e.g., a rubbed polyimide surface) and that can be appropriately blocked.

In preferred embodiments, the device is configured so that the substrate (and hence the surface of the substrate) can be contacted with a liquid crystal. Accordingly, in some embodiments, the device comprises a chamber that contains the liquid crystal. In some embodiments, the chamber is open and formed by walls extending from the surface of the substrate. For example, the substrate can be the bottom surface of a well in a multiwell plate (e.g., a 96 well plate) and the chamber is formed by the walls of the well. In other embodiments, the chamber is formed by at least a second substrate arranged opposite to the first substrate to form an optical cell. In some preferred embodiments, the two substrates of the optical cell are separated by a spacer (e.g., a polymer film). In some embodiments, the second substrate is also treated or fabricated so that it orients liquid crystals, while in other embodiments, the second substrate has no effect on the orientation of the liquid crystal. In some preferred embodiments, the devices further comprise channels through which liquid crystal, sample solution (i.e., a solution suspected of containing an analyte) can be delivered to the first substrate surface or the chamber.

In some embodiments, the devices of the present invention comprise a plurality of assay regions. In some embodiments, the assay regions are arrayed on the first substrate surface. In some embodiments, the assay regions are separated so that separate chambers are are formed (e.g., a 98 well format), while in other embodiments the assay regions are located within a single chamber. In this manner, the devices of the present invention are useful for multiplexed assays.

In some embodiments, the devices are configured for reading with an optical (bar code scanner). Accordingly, in further embodiments, a series of parallel lines or bars is printed on the back face of the optical cell, running parallel to a detection region, and a simple bar code reader is used to quantify and store information about the extent of the disrupted liquid crystal front at the time of reading.

In some embodiments, an optical cell is formed for detecting organophosphate compounds (see, e.g., U.S. application Ser. No. 10/897,626, incorporated herein by reference in its entirety). In these devices, airborne pesticide diffuses in from the open edge of an optical cell, and upon binding to the top and bottom coated glass surfaces, the pesticide disrupts homeotropically aligned liquid crystals in proportion to 1) the concentration of the pesticide in the outside air and 2) the time of exposure. In further embodiments, opposite edges of an optical cell are both open to the outside atmosphere; and a pesticide diffuses in from opposite edges of an optical cell towards the center of the cell. The disrupted liquid crystal region progresses as a discrete, uniform, advancing front, forming a relatively linear demarcation between disrupted liquid crystal behind the front and homeotropically aligned liquid crystal ahead of the front. In further embodiments, a series of parallel lines or bars is printed on the back face of the optical cell, running parallel to the flow front, and a simple bar code reader is used to quantify and store information about the extent of the disrupted liquid crystal front at the time of reading, and hence, the pesticide concentration detected. As the disrupted liquid crystal front progresses with time of exposure, more bars become visible. The exposed bars correspond to the pesticide concentration and time of exposure. A standard bar code identification sequence is printed on the top surface of the optical cell housing, in a location neighboring the optical cell itself. Scanning the device with a bar code reader simultaneously identifies the device serial number and measures the signal intensity. In the absence of a bar code reader, the number of lines visible after exposure could be visually counted in order to quantify the extent of the disrupted liquid crystal front, and hence the concentration of pesticide or other analyte being measured in the optical cell could be measured without a dedicated instrument.

VIII. Kits

In some embodiments, the present invention provides kits for the detection of analytes. In preferred embodiments, the kits comprise one or more substrates as described in detail above. In some embodiments, the kits comprise capture and detection substrates. In some preferred embodiments, the capture substrates are beads or stamps. In further embodiments, the kits comprise a substrate that can be used in conjunction with the detection substrate to assemble a liquid crystal cell. In some embodiments, the kits comprise a vial containing mesogens. In still other embodiments, the kits comprise at least one vial containing a control analyte or analytes. In still other embodiments, the kit comprises instructions for using the reagents contained in the kit for the detection of at least one type of analyte. In some embodiments, the instructions further comprise the statement of intended use required by the U.S. Food and Drug Administration (FDA) in labeling in vitro diagnostic products. The FDA classifies in vitro diagnostics as medical devices and requires that they be approved through the 510(k) procedure. Information required in an application under 510(k) includes: 1) The in vitro diagnostic product name, including the trade or proprietary name, the common or usual name, and the classification name of the device; 2) The intended use of the product; 3) The establishment registration number, if applicable, of the owner or operator submitting the 510(k) submission; the class in which the in vitro diagnostic product is placed under section 513 of the FD&C Act, if known, its appropriate panel, or, if the owner or operator determines that the device has not been classified under such section, a statement of that determination and the basis for the determination that the in vitro diagnostic product is not so classified; 4) Proposed labels, labeling and advertisements sufficient to describe the in vitro diagnostic product, its intended use, and directions for use. Where applicable, photographs or engineering drawings should be supplied; 5) A statement indicating that the device is similar to and/or different from other in vitro diagnostic products of comparable type in commercial distribution in the U.S., accompanied by data to support the statement; 6) A 510(k) summary of the safety and effectiveness data upon which the substantial equivalence determination is based; or a statement that the 510(k) safety and effectiveness information supporting the FDA finding of substantial equivalence will be made available to any person within 30 days of a written request; 7) A statement that the submitter believes, to the best of their knowledge, that all data and information submitted in the premarket notification are truthful and accurate and that no material fact has been omitted; 8) Any additional information regarding the in vitro diagnostic product requested that is necessary for the FDA to make a substantial equivalency determination.

EXAMPLES

Example 1

Biotinylated Liquid Crystal

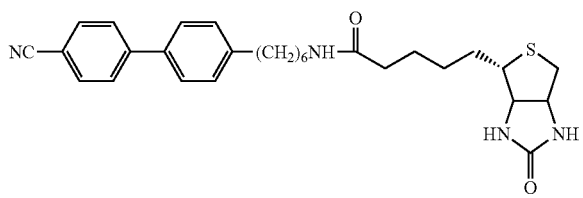

1,4-dibromobenzene is dissolved in dry tetrahydrofuran. The solution is cooled with liquid nitrogen. One equivalent of hexyl lithium is added to the solution under argon. The resulting lithium solution is added dropwise to another dry tetrahydrofuran solution containing five molar equivalents of 1,6-dibromohexane. The solvent is evaporated, and the crude 1-bromo-4-(6-bromohexyl)benzene is purified by silica gel column chromatography, 1 to 5% EtOAc in hexane. The 1-bromo-4-(6-bromohexyl)benzene is dissolved in dry dimethylformamide and potassium phthalimidate is added. The dimethylformamide is remove under vacuum, and the crude product is taken up in methylene chloride. The solution is washed with water several times, dried with magnesium sulfate, and the solvent is evaporated to give the phthalimide protected amino alkyl aryl bromide (i.e., N-[6-(4'-bromophenyl)hexyl]-phthalimide.

The Suzuki Coupling is accomplished according to Arvela et al., J. Org. Chem., 70 (1), 161-168, 2005. In a 10 mL glass tube are placed aryl halide (2-[6-(4-bromophenyl)hexyl]-1H-isoindole-1,3(2H)-dione), arylboronic acid (4-cyanophenyl-boronic acid), $Na_2CO_3$ (392 mg, 3.7 mmol), tetrabutylammonium bromide (322 mg, 1.0 mmol), aliquots of a 10 ppm solution of $Pd(OAc)_2$. The vessel is sealed with a septum, shaken vigorously, and placed into the microwave cavity. Microwave irradiation of 150 W is used, the temperature being ramped from room temperature to 150° C. Once this temperature is reached, the reaction mixture is held at this temperature for 5 min. After allowing the mixture to cool to room temperature, the reaction vessel is opened and the contents poured into a separating funnel. Water and ethyl acetate are added, and the organic material is extracted and removed. After further extraction of the aqueous layer with ether, combining the organic washings and drying them over $MgSO_4$, the ethyl acetate is removed in vacuo leaving the product. The product is purified and isolated by chromatography using hexane/ethyl acetate as eluent.

The phthalimide is dissolved in ethanol and hydrazine is added. After heating and stirring for several days the solution is cooled and the solids are removed by filtration. The filtrate is dissolved in methylene chloride and extracted with 0.1N HCl. The aqueous extracts are washed once with methylene chloride, made basic with 5% NaOH, and extracted with methylene chloride. Removal of the solvent under vacuum gives the free amine. N-(Biotinyloxy)succinimide or Biotin p-nitrophenyl ester and the free amine are dissolved in acetonitrile and water. After stirring, the acetonitrile is removed under vacuum and the product is extracted into methylene chloride, combining the organic washings and drying them over $MgSO_4$, the methylene chloride is removed in vacuo leaving the product.

A mixed liquid crystal is made containing:

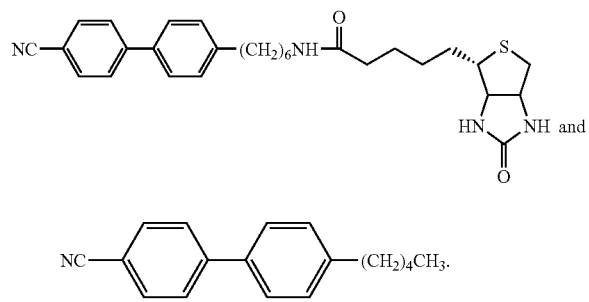

The liquid crystal composition is homogenized by heating at about 110° and by shaking, then allowed to cool down to room temperature. An empty 25 micrometer thick liquid crystal containment structure is fabricated by sealing two indium tin oxide ("ITO") (transparent electrodes) glass coated slides. One of the ITO slides contains a thin coat of gold on the surface. This surface is exposed to 2-mercaptoethylamine followed by avidin. A small hole is kept in the sealing to be used for filling the liquid crystal composition. The containment structure is vacuum filled with the above liquid crystal composition, pressed and sealed.

Example 2

Metal Salt Copper, Indium, and Chromium Perchlorate to a Liquid Crystal Such 5CB in Order to Orient the Liquid Crystal Upon Binding to a Surface A mixed liquid crystal is made containing indium perchlorate octahydrate:

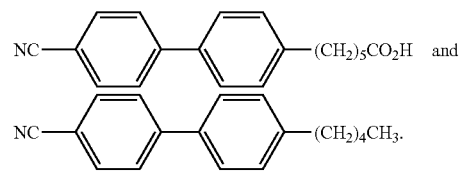

The liquid crystal composition is homogenized by heating at about 110° and by shaking, then allowed to cool down to room temperature. An empty 25 micrometer thick liquid crystal containment structure is fabricated by sealing two indium tin oxide ("ITO") (transparent electrodes) glass coated slides. A small hole is kept in the sealing to be used for filling the liquid crystal composition. The containment structure is vacuum filled with the above liquid crystal composition, pressed and sealed.

Example 3

Disodium Cromoglycate Liquid Crystal with HIV Recognition Moiety

In AIDS Res. Hum. Retroviruses 19 (7), 597-607 (2003) the reference discloses anti-HIV-1 gp120 immunoglobulin light and heavy chain variable regions. The following protein is anti-HIV-1 gp120 immunoglobulin light chain variable region with lysine starter linker (KLLLLLLLL): KLLLLLLLLL NSCWTQSPSS LSASVGDRVT ITCQASQDIS NYLNWYQHKP GKAPKLLIYT ASNLETGVPS RFSGGGSGTH FSFTITSLQP EDAATYFCQQ YDNLGDLSFG GGTKVEIKR. The following protein is anti-HIV-1 gp120 immunoglobulin heavy chain variable region with lysine starter linker (KLLLLLLLL): KLLLLLLLLL QVQLVQSGGG LVQPGGSLRL SCAAFGFNFS SYVMHWVRQA PGKGLEYLSA ISSDGETTYH ANSVKGRFTS SRDNSKNTLF LQMGSLRTED VAVYYCARDR YYETSGSNAF DVWGQGTMVV VSS. Both sequence are made by expression in *E. coli* with GST using appropriate DNA sequence. The GST is removed by exposure to thrombin.

Chromoglicic acid that is 5,5'-[(2-hydroxy-1,3-propanediyl)bis(oxy)]bis[4-oxo-4H-1-benzopyran-2-carboxylic acid] is mixed in pentanol and dioxane (FIG. 2). A few drops of concentrated sulfuric acid are added. The mixture is heated and then cooled to room temperature. The crude product is extracted between 0.1 N aqueous sodium hydroxide and methylene chloride. The aqueous layer is washed twice more with methylene chloride, and made acidic by the addition of 1 N aqueous hydrogen chloride. The monocarboxylic acid is extracted in to methylene chloride and purified by silica gel column chromatography (ethyl acetate/acetic acid/hexane).

Dissolve the monocarboxylic acid and bromo-tris-pyrrolidino-phosphonium hexafluorophosphate in dimethylformamide. Add diisopropyl ethylamine, mix and add immediately to HOBt-6-carboxamidomethyl polystyrene (Novabiochem). Leave to react for 5 hours with gentle agitation. Wash resin with DMF and repeat reaction with fresh reagents. After, rewash resin with dimethylformamide. Suspend resin in dimethylforamide, add protein with lysine starter linker and allow to react with gentle agitation. Remove resin by filtration, wash and evaporate the combined filtrates to dryness.

A mixed liquid crystal in made containing:

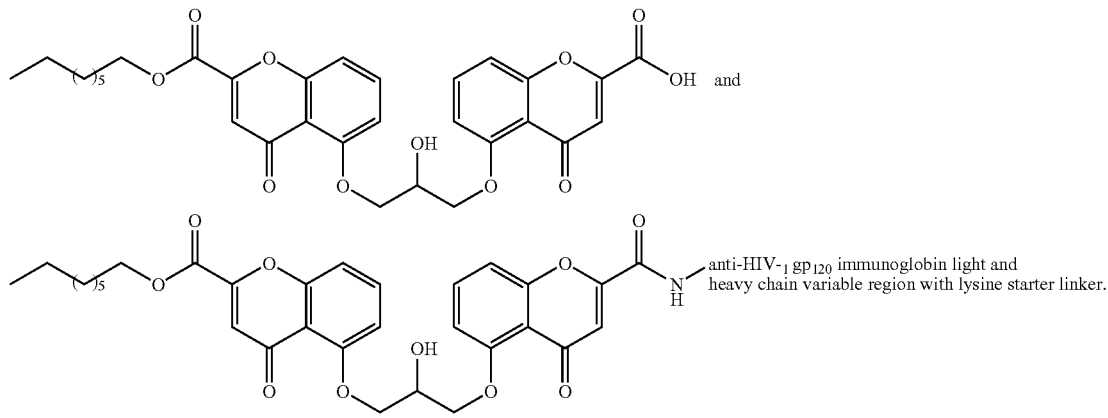

The liquid crystal composition is homogenized by heating at about 110° and by shaking, then allowed to cool down to room temperature. An empty 25 micrometer thick liquid crystal containment structure is fabricated by sealing two indium tin oxide ("ITO") (transparent electrodes) glass coated slides. A small hole is kept in the sealing to be used for filling the liquid crystal composition. The containment structure is vacuum filled with the above liquid crystal composition, pressed and sealed.

Example 4

Lysozyme Liquid Crystal where Biotinylate Lysozyme Orientates the Liquid Crystal Through Biotin Interaction with Avidin Lysozyme has the following sequence: KVFGRCELAA AMKRHGLDNY RGYSLGNWVC AAKFESNFNT QATNRNTDGS TDYGILQINS RWWCNDGRTP GSRNLCNIPC SALLSSDITA SVNCAKKIVS DGNGMNAWVA WRNRCKGTDV QAWIRGCRL. The protein is synthetically produced using solid phase Fmoc procedures. Preferably, 10 amino acid sequences are coupled together. The first amino acid terminal Lysine (K) is biotinylated by using N-α-Fmoc-N-∈-biotinyl-L-lysine (Novabiochem). An empty 25 micrometer thick liquid crystal containment structure is fabricated by sealing two indium tin oxide ("ITO") (transparent electrodes) glass coated slides. One of the ITO slides contains a thin coat of gold on the surface. This surface is exposed to 2-mercaptoethylamine followed by avidin. A small hole is kept in the sealing to be used for filling the liquid crystal composition. The containment structure is vacuum filled with the above liquid crystal composition, pressed and sealed.

Example 5

Figure 3:
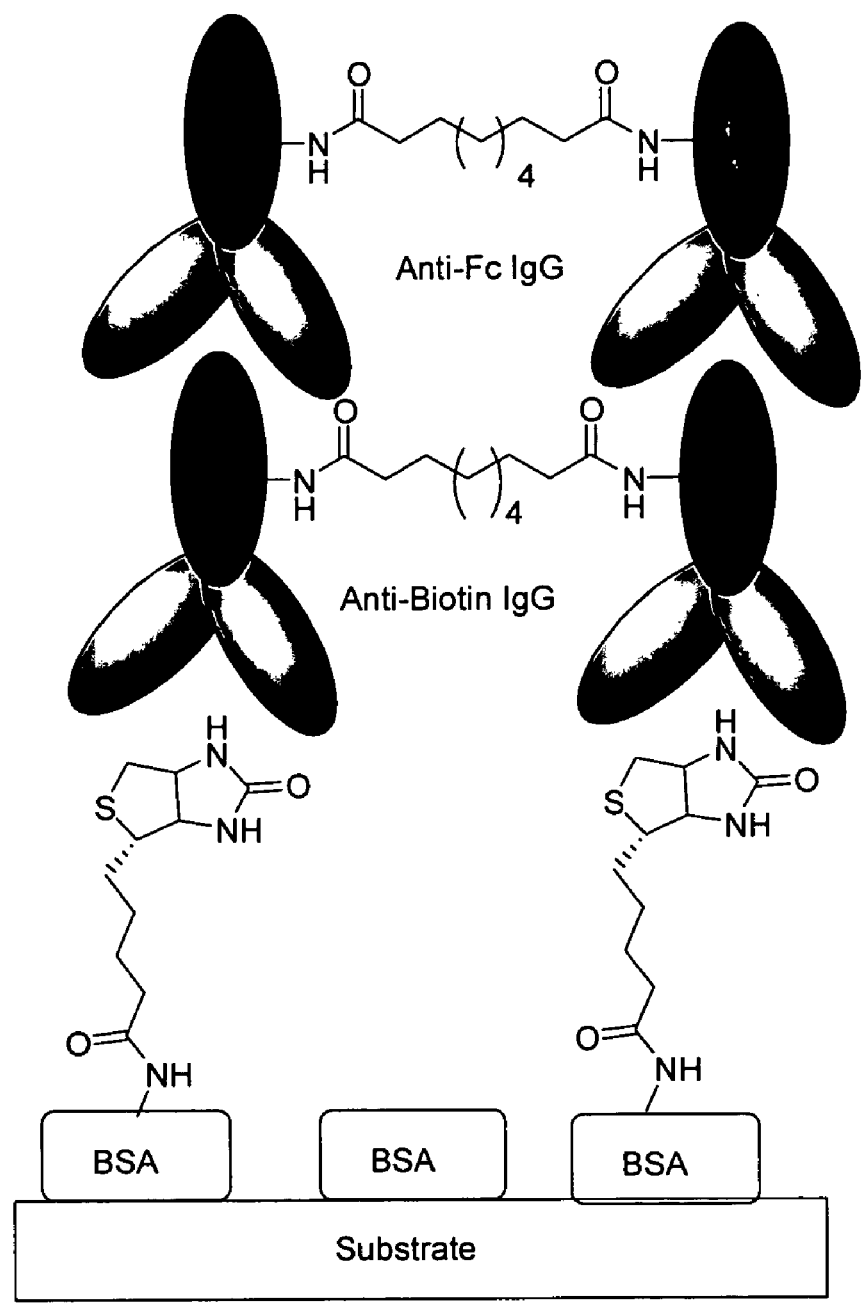
FIG. 3. This is a pictorial representation of a biotinylated bovine serum album orientating antibodies in a liquid crystal and subsequently linking them together.
Figure 4:
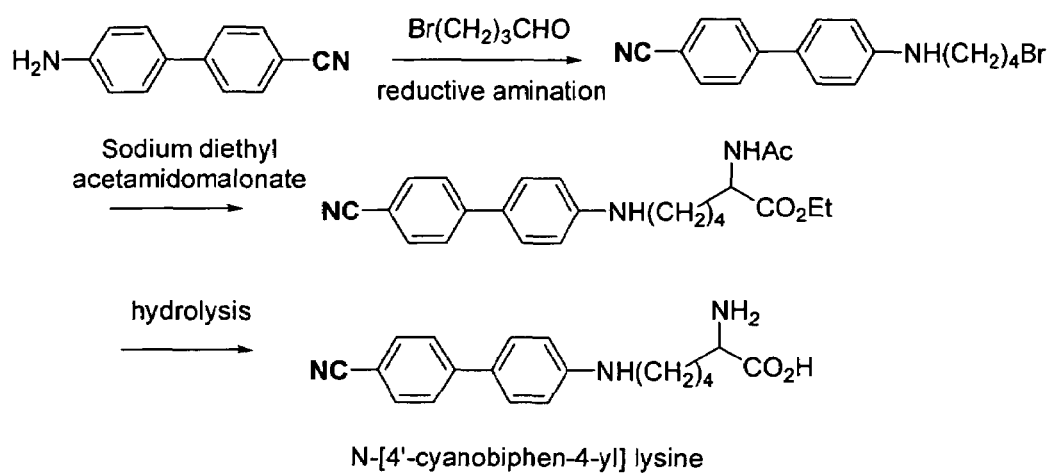
FIG. 4. This is a scheme for the preparation of an amino acid coupled to a mesogen to form 4'-cyanobiphen-4-yllysine.
Figure 5:
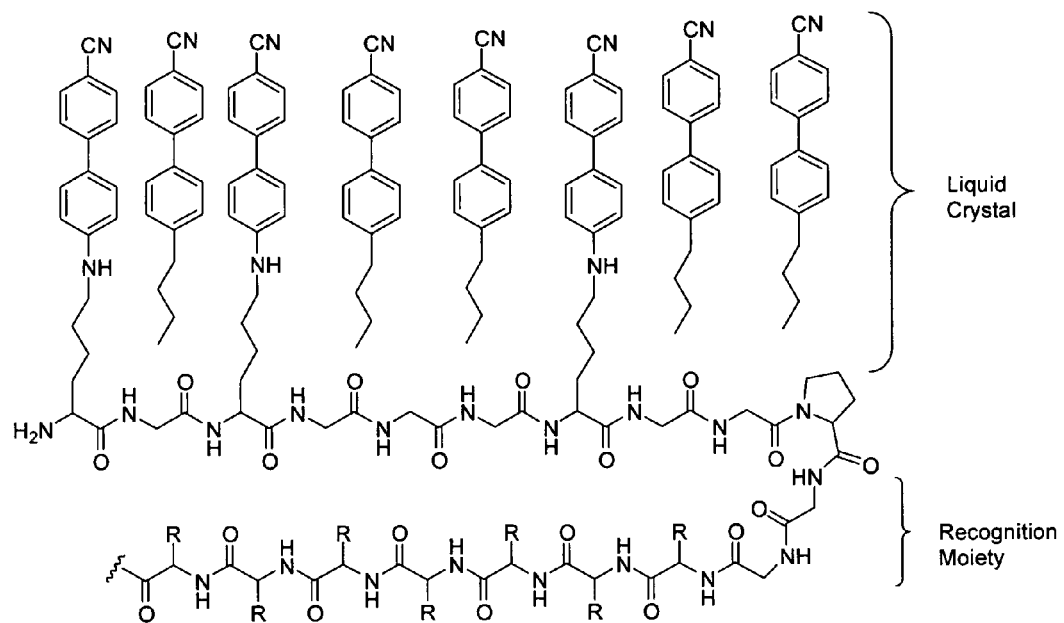
FIG. 5. This is a pictorial representation of a liquid crystal protein containing a recognition moiety.

Amplify Liquid Crystal Alignment by Creating Elongated Structures in the Liquid Crystal A film of biotinylated bovine serum albumin (BSA) is covalently immobilized on the surface of glass microscope-slides and mechanically rubbed using a cloth as describe in Kim et al., Anal Chem 2000 72(19): 4646-53. Anti-Biotin IgG is dissolved in 5,5'-[(2-hydroxy-1,3-propanediyl)bis(oxy)]bis[4-oxo-4H-1-benzopyran-2-carboxylic acid]. The film of biotinylated (BSA) is used as a substrate for a liquid crystal made with the mixture of anti-biotin IgG and 5,5'-[(2-hydroxy-1,3-propanediyl)bis(oxy)]bis[4-oxo-4H-1-benzopyran-2-carboxylic acid]. Anti-Fc IgG followed by the Bis N-oxysuccinimidate of docecanedicarboxylic acid (FIG. 3) is placed on the surface of the liquid crystal linking adjacent IgGs and locking them into the conformation of the surrounding liquid crystal matrix.

Example 7

Process for Producing 4'-cyanobiphen-4-yllysine

4'-amino-(1,1'-Biphenyl)-4-carbonitrile is dissolved in dimethyl formamide. Sodium hydride is added to the solution followed by 4-bromo-1-hydroxybutane to provide 4'-(4-hydroxybutylamino)-(1,1'-Biphenyl)-4-carbonitrile. 4'-(4-hydroxybutylamino)-(1,1'-Biphenyl)-4-carbonitrile is suspended in dichloromethane.

Phosphorous tribromide is added dropwise. After 4 h of stirring the reaction mixture is extracted with ice-cold water and subsequently with saturated aqueous $NaHCO_3$. The organic phase is dried over $MgSO_4$ and evaporated to dryness in vacuo. The remaining is added to a freshly made solution of sodium diethyl acetamidomalonate (prepared by treatment of diethyl acetamidomalonate with sodium hydride in dry tetrahydrofuran and subsequent filtration of the salt and drying in vacuo in dry $Me_2SO$) and stirred at room temperature under nitrogen. The reaction mixture is taken into water and extracted with ethyl acetate. The organic phase is dried over $Na_2SO_4$ and evaporated to dryness in vacuo. With this is added lithium chloride dissolved in a mixture of water and N,N-dimethylformamide and heated to 140° C. The solvent is then removed in vacuo, and the residue is taken up in water. The aqueous phase is extracted with ethyl acetate, and the combined organic phases are dried over $Na_2SO_4$ and evaporated to dryness in vacuo. With this is added a mixture of $Me_2SO$ and phosphate buffer (pH 7.5). Carlsberg subtilisin is added, and the mixture is stirred overnight at room temperature. Water is added, and non-reacted ethyl ester (D or L-form) is removed by extraction with ethyl acetate. The pH of the aqueous phase is adjusted to 2.5 by the addition of diluted HCl and extracted with ethyl acetate. The organic phase is evaporated in vacuo to an oil, which is dissolved in water and freeze-dried. With this is added 5 N HCl and heated under reflux. After cooling, the solvent is removed in vacuo.

Example 8

Process for Producing 4'-cyanobiphen-4-ylalanine

4'-Hydroxymethyl-(1,1'-Biphenyl)-4-carbonitrile is suspended in dichloromethane. Phosphorous tribromide is added dropwise. After 4 hours of stirring the reaction mixture is extracted with ice-cold water and subsequently with saturated aqueous $NaHCO_3$. The organic phase is dried over $MgSO_4$ and evaporated to dryness in vacuo. The remaining is added to a freshly made solution of sodium diethyl acetamidomalonate (prepared by treatment of diethyl acetamidomalonate with sodium hydride in dry tetrahydrofuran and subsequent filtration of the salt and drying in vacuo in dry $Me_2SO$) and stirred for at room temperature under nitrogen. The reaction mixture is taken into water and extracted with ethyl acetate. The organic phase is dried over $Na_2SO_4$ and evaporated to dryness in vacuo. With this is added lithium chloride dissolved in a mixture of water and N,N-dimethylformamide and heated to 140° C. The solvent is then removed in vacuo, and the residue is taken up in water. The aqueous phase is extracted with ethyl acetate, and the combined organic phases are dried over $Na_2SO_4$ and evaporated to dryness in vacuo. With this is added a mixture of $Me_2SO$ and phosphate buffer (pH 7.5). Carlsberg subtilisin is added, and the mixture is stirred overnight at room temperature. Water is added, and non-reacted ethyl ester (D or L-form) is removed by extraction with ethyl acetate. The pH of the aqueous phase is adjusted to 2.5 by the addition of diluted HCl and extracted with ethyl acetate. The organic phase is evaporated in vacuo to an oil, which is dissolved in water and freeze-dried. With this is added 5 N HCl and heated under reflux. After cooling, the solvent is removed in vacuo.

Example 9 tRNA$^{Phe}$ Charged with 4'-cyanobiphen-4-ylalanine by Aminoacylation with Mutant Phenylalanine tRNA Synthetase Wild type and αA294G *E. coli* PheRS are purified, and pyrophosphate ($PP_i$) exchange and aminoacylation reactions are performed as described in Ibba et al., (1994) Biochemistry 33, 7107-7112 and Bentin et al., J. Biol. Chem., 279:19, 19839-19845 (2004), with unlabeled 4'-cyanobiphen-4-ylalanine. The direct attachment of 4'-cyanobiphen-4-ylalanine to in vitro transcribed tRNA is monitored by direct $^{32}$P labeling of TRNA$^{Phe}$ using *E. coli* tRNA-terminal nucleotidyltransferase as described in Seth, et al., (2002) Biochemistry 41, 4521-4532 followed by aminoacylation and product visualization as previously described in Wolfson, A. D., and Uhlenbeck, O. C. (2002) Proc. Natl. Acad. Sci. U.S.A. 99, 5965-5970.

Protein purification is done as described in Sharma et al., (2000) FEBS Lett 467, 37-40, with M9 minimal media cultures supplemented with 19 amino acids and 4'-cyanobiphen-4-ylalanine or phenylalanine as described in Datta, D. et al., (2002) J. Am. Chem. Soc. 124, 5652-5653 and using nickel nitrilotriacetic acid chromatography spin columns under denaturing conditions. Buffer exchange from 8 M urea, 100 mm sodium phosphate, pH 4.5, into water is done using Amicon 10-kDa cutoff ultrafiltration spin filters.

Example 10 tRNA$^{pyrrolysine}$ Charged with 4'-cyanobiphen-4-yllysine by Aminoacylation with pylS Gene Aminoacyl-tRNA Synthetase The pylT gene, which encodes transfer RNA (tRNA$^{ply}$) with a CUA anticodon and the pylS gene and variants thereof that encodes a class II aminoacyl-tRNA synthetase capable of charging tRNA$^{pyl}$ with 4'-cyanobiphen-4-yllysine is incorporated in to a *E. coli* genome. Additionally, DNA that will express the following protein sequence $A_{CBLYS}^{LC}$GG-GA$_{CBLYS}^{LC}$GGGA$_{CBLYS}^{LC}$G GGPGGGGGGG QIVLTQSPAI MSASPGEKVT MTCSASSSVS SRYLHWYQQK SEASPKLWIY GTSNLASGVP ARFSGSGSGT SYSLTVSSVE AEDAATYYCQ QYHSDPYTFG SGTKLEIKR, wherein the letters designate the generally accepted single letter amino acid code except $A_{CBLYS}^{LC}$ is 4'-cyanobiphen-4-yllysine, is incorporated into the *E. coli* genome for expression, wherein the codon for $A_{CBLYS}^{LC}$ is the complement to anticodon CUA for 4'-cyanobiphen-4-yllysine charged tRNA$^{pyl}$. Protein purification is done as described in Sharma et al., (2000) FEBS Lett 467, 37-40, of M9 minimal media cultures supplemented with 19 amino acids and 4'-cyanobiphen-4-yllysine appropriately adapted as described in Datta, D. et al., (2002) J. Am. Chem. Soc. 124, 5652-5653.

Example 11

Protein Liquid Crystal with Insulin Recognition Moiety

A mixed liquid crystal is made containing 3CB and $A_{CBLYS}^{LC}$GGG$_{ACBLYS}^{LC}$GGGA$_{CBLYS}^{LC}$GGG PGGGGGGG QIVLTQSPAI MSASPGEKVT MTCSASSSVS SRYLHW-YQQK SEASPKLWIY GTSNLASGVP ARFSGSGSGT SYSLTVSSVE AEDAATYYCQ QYHSDPYTFG SGT-KLEIKR wherein the letters designate the generally accepted single letter amino acid code except $A_{CBLYS}^{LC}$ is 4'-cyanobiphen-4-yllysine.

The liquid crystal composition is homogenized by heating at about 110° and by shaking, then allowed to cool down to room temperature. An empty 25 micrometer thick liquid crystal containment structure is fabricated by sealing two indium tin oxide ("ITO") (transparent electrodes) glass coated slides. The top slide contains a hole exposing the area within the hole of the liquid crystal. A sample solution containing insulin is place by the hole in the slide. The liquid crystal is observed between crossed polarizers.

Example 13

Detection Based on Bar Code Reader

An airborne pesticide diffuses in from the open edge of an optical cell, and upon binding to the top and bottom coated glass surfaces, it disrupts homeotropically aligned LC in proportion to 1) the concentration of the pesticide in the outside air and 2) the time of exposure. The disrupted liquid crystal region progresses as a discrete, uniform, advancing front, forming a relatively linear demarcation between disrupted liquid crystal behind the front and homeotopically aligned liquid crystal ahead of the front. A series of parallel lines or bars is printed on the back face of the optical cell, running parallel to the flow front, a bar code reader is used to quantify and store information about the extent of the disrupted liquid crystal front at the time of reading, and hence, the pesticide concentration detected. As the disrupted liquid crystal front progresses with time of exposure, more bars become visible. The number of exposed bars corresponds to the pesticide concentration and time of exposure. A bar code identification sequence is printed on the top surface of the optical cell housing, in a location neighboring the optical cell itself. Scanning the device with a bar code reader simultaneously identifies the device serial number and measure the signal intensity.

The invention claimed is:

1. A compound comprising a recognition moiety covalently attached to a mesogen substituent, wherein said recognition moiety is a protein.

2. The compound of claim 1, wherein said mesogen is an organic molecule.

3. The compound of claim 1, wherein said mesogen is selected from the group consisting of 5,5'-[(2-hydroxytrimethylene)dioxy]bis(4-oxo-4H-1-benzopyran-2-carboxylic acid), 4'-alkyl-(1,1'-Biphenyl)-4-carbonitrile, and 5,5'-[(2-hydroxytrimethylene)dioxy]bis(4-oxo-4H-1-benzopyran-2-carboxylic acid).

4. A compound of claim 1, wherein the mesogen is an amino acid sequence.

5. A device comprising the compound of claim 1.

6. The device of claim 5, wherein said device comprises a substrate having a surface in contact with said compound.

7. The device of claim 6, wherein said surface is anisotropic.

8. A liquid crystal composition comprising a plurality of compounds comprising a protein recognition moiety covalently attached to a mesogen substituent.

9. The composition of claim 8, wherein the mesogen is selected from the group consisting of 5,5'-[(2-hydroxytrimethylene)dioxy]bis(4-oxo-4H-1-benzopyran-2-carboxylic acid), 4'-alkyl-(1,1'-Biphenyl)-4-carbonitrile and 5,5'-[(2-hydroxytrimethylene)dioxy]bis(4-oxo-4H-1-benzopyran-2-carboxylic acid).

10. The composition of claim 8, further comprising a metal salt.

11. A liquid crystal composition of claim 10, wherein said metal is selected from the group consisting of copper, indium, and chromium.

12. A device comprising the composition of claim 8.

13. A method comprising:
a) providing the device of claim 12 and a sample suspected of containing an analyte that is capable of interacting with said recognition moiety;
b) contacting said device with said sample, wherein a change in the orientation of said liquid crystal composition is indicative of the presence of said analyte.

* * * * *